US012575863B2

(12) United States Patent
Harris et al.

(10) Patent No.: US 12,575,863 B2
(45) Date of Patent: Mar. 17, 2026

(54) INTERSPINOUS-INTERLAMINAR STABILIZATION SYSTEMS AND METHODS

(71) Applicant: FloSpine, LLC, Boca Raton, FL (US)

(72) Inventors: Peter M. Harris, Boca Raton, FL (US); Luis A. Escobar, III, Boca Raton, FL (US)

(73) Assignee: FloSpine, LLC, Boca Raton, FL (US)

( * ) Notice: Subject to any disclaimer, the term of this patent is extended or adjusted under 35 U.S.C. 154(b) by 23 days.

(21) Appl. No.: 18/440,828

(22) Filed: Feb. 13, 2024

(65) Prior Publication Data

US 2024/0268869 A1 Aug. 15, 2024

Related U.S. Application Data

(60) Provisional application No. 63/445,253, filed on Feb. 13, 2023.

(51) Int. Cl.
*A61B 17/70* (2006.01)

(52) U.S. Cl.
CPC ...... *A61B 17/7067* (2013.01); *A61B 17/7047* (2013.01); *A61B 17/7065* (2013.01)

(58) Field of Classification Search
CPC ............ A61B 17/7067; A61B 17/7047; A61B 17/7065; A61B 17/7068; A61B 17/7062; A61B 17/7071
See application file for complete search history.

(56) References Cited

U.S. PATENT DOCUMENTS

| | | | |
|---|---|---|---|
| 5,645,599 A | 7/1997 | Samani | |
| 6,126,689 A | 10/2000 | Brett | |
| 6,443,989 B1 | 9/2002 | Jackson | |
| 6,666,891 B2 | 12/2003 | Boehm, Jr. et al. | |

(Continued)

FOREIGN PATENT DOCUMENTS

RU 2322212 C1 4/2008

OTHER PUBLICATIONS

Globus Medical Launches AERIAL, An Expandable Interspinous Fixation Device—Covering the specialized field of orthopedic product development and manufacturing (odtmag.com), May 31, 2019.

*Primary Examiner* — Tracy L Kamikawa
(74) *Attorney, Agent, or Firm* — David Meibos; Maywood IP Law

(57) ABSTRACT

A system may be configured to maintain spacing between a superior spinous process and a superior lamina, and an inferior spinous process and an inferior lamina, of adjacent vertebrae of a spine. The system may include an implant that includes two superior wings that extend superiorly from a proximal superior surface such that, in an implanted position, the superior spinous process may be engaged therebetween. The implant may also include two inferior wings that extend inferiorly from a proximal inferior surface such that, in the implanted position, the inferior spinous process may be engaged therebetween. The system may include a clamp that includes two superior arms configured to engage the two superior wings to prevent disengagement of the two superior wings from the superior spinous process and two inferior arms configured to engage the two inferior wings to prevent disengagement of the two inferior wings from the inferior spinous process.

19 Claims, 16 Drawing Sheets

(56)                References Cited

U.S. PATENT DOCUMENTS

| | | | |
|---|---|---|---|
| 6,761,720 B1 * | 7/2004 | Senegas ............. | A61B 17/7053 |
| | | | 606/249 |
| 7,635,378 B2 * | 12/2009 | Zucherman ........ | A61B 17/7065 |
| | | | 606/248 |
| 7,674,296 B2 | 3/2010 | Rhoda et al. | |
| 7,763,074 B2 | 7/2010 | Altarac et al. | |
| 7,922,750 B2 | 4/2011 | Trautwein et al. | |
| 8,012,207 B2 | 9/2011 | Kim | |
| 8,123,782 B2 | 2/2012 | Altarac et al. | |
| 8,123,807 B2 | 2/2012 | Kim | |
| 8,128,662 B2 | 3/2012 | Altarac et al. | |
| 8,152,837 B2 | 4/2012 | Altarac et al. | |
| 8,439,951 B2 | 5/2013 | Trautwein et al. | |
| 8,623,056 B2 * | 1/2014 | Linares ............. | A61B 17/7068 |
| | | | 606/248 |
| 8,945,184 B2 | 2/2015 | Hess et al. | |
| 9,060,876 B1 | 6/2015 | To et al. | |
| 9,211,147 B2 * | 12/2015 | Gordon ............. | A61B 17/7068 |
| 9,314,276 B2 | 4/2016 | Hess et al. | |
| 9,370,382 B2 | 6/2016 | Thalgott et al. | |
| 9,402,733 B1 | 8/2016 | To | |
| 9,750,552 B2 | 9/2017 | Stephan et al. | |
| 9,907,581 B2 | 3/2018 | Hess et al. | |
| 9,907,671 B2 | 3/2018 | Fessler | |
| 9,968,381 B2 | 5/2018 | Thalgott et al. | |
| 9,993,350 B2 | 6/2018 | Cain | |
| 10,278,745 B2 * | 5/2019 | Woodworth ....... | A61B 17/7071 |
| 10,398,478 B2 | 9/2019 | Ganter et al. | |
| 10,512,550 B2 | 12/2019 | Bechtel et al. | |
| 10,695,189 B2 | 6/2020 | Li et al. | |
| 11,234,740 B2 | 2/2022 | Frock et al. | |

| | | | |
|---|---|---|---|
| 11,311,388 B2 | 4/2022 | Frock et al. | |
| 11,311,389 B2 | 4/2022 | Frock et al. | |
| 11,534,310 B2 | 12/2022 | Frock et al. | |
| 11,801,075 B2 | 10/2023 | Frock et al. | |
| 2002/0143401 A1 | 10/2002 | Michelson | |
| 2004/0181282 A1 | 9/2004 | Zucherman | |
| 2005/0113916 A1 | 5/2005 | Branch | |
| 2006/0122701 A1 | 6/2006 | Kiester | |
| 2007/0219634 A1 | 9/2007 | Greenhalgh | |
| 2007/0233083 A1 | 10/2007 | Abdou | |
| 2008/0015693 A1 | 1/2008 | Le Couedic | |
| 2008/0183204 A1 | 7/2008 | Greenhalgh et al. | |
| 2008/0281423 A1 | 11/2008 | Sheffer et al. | |
| 2008/0319549 A1 | 12/2008 | Greenhalgh et al. | |
| 2009/0198337 A1 | 8/2009 | Phan | |
| 2009/0281628 A1 | 11/2009 | Oglaza | |
| 2009/0297603 A1 | 12/2009 | Joshi | |
| 2010/0106190 A1 | 4/2010 | Linares | |
| 2011/0040330 A1 | 2/2011 | Sheffer | |
| 2011/0106163 A1 | 5/2011 | Hochschuler et al. | |
| 2012/0226312 A1 | 9/2012 | Thalgott et al. | |
| 2013/0184754 A1 | 7/2013 | Taber | |
| 2013/0345753 A1 * | 12/2013 | Kretzer ............. | A61B 17/7049 |
| | | | 606/279 |
| 2014/0039629 A1 | 2/2014 | Cipoletti et al. | |
| 2014/0288653 A1 | 9/2014 | Chen | |
| 2016/0113686 A1 | 4/2016 | Zappacosta et al. | |
| 2016/0228157 A1 | 8/2016 | Shoshtaev | |
| 2016/0270827 A1 | 9/2016 | Sheffer et al. | |
| 2017/0020582 A1 | 1/2017 | Asfora | |
| 2017/0079695 A1 | 3/2017 | Zappacosta et al. | |
| 2018/0263667 A1 | 9/2018 | Dinville | |
| 2019/0083145 A1 | 3/2019 | Trautwein | |
| 2022/0249135 A1 | 8/2022 | Soo | |

* cited by examiner

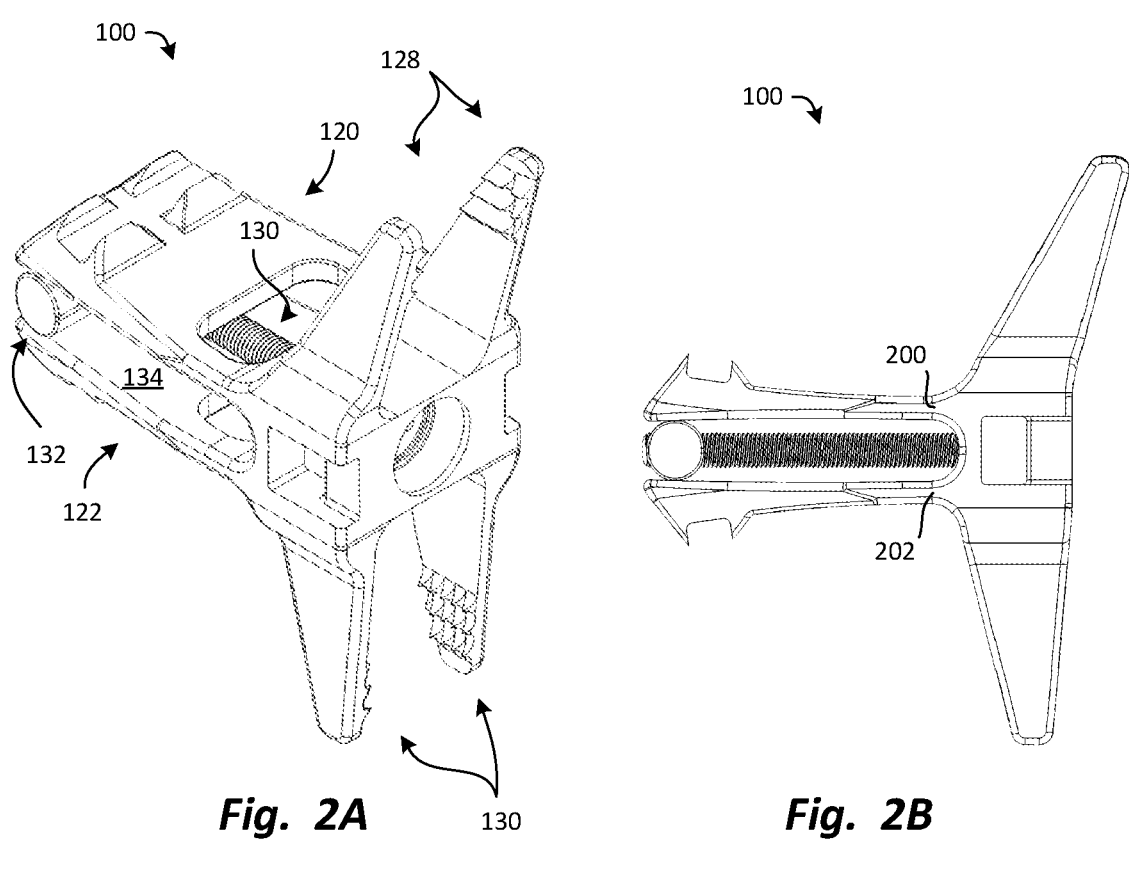
Fig. 2A
Fig. 2B
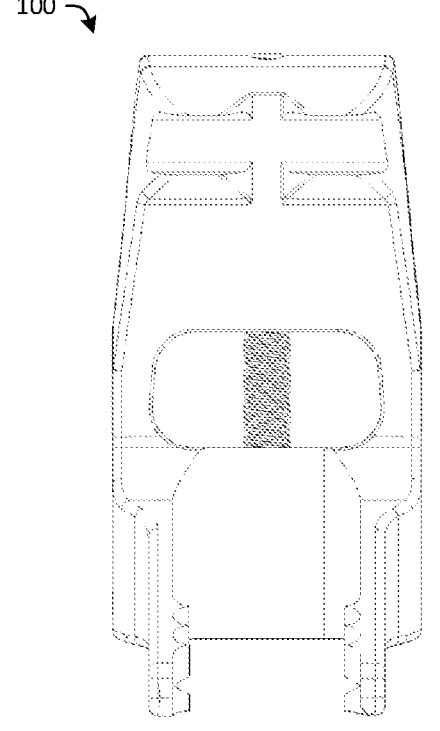
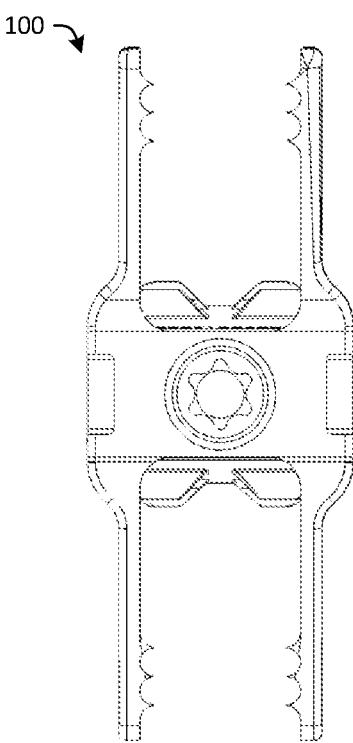
Fig. 2C
Fig. 2D

1100

1100

SECTION A-A

SECTION A-A

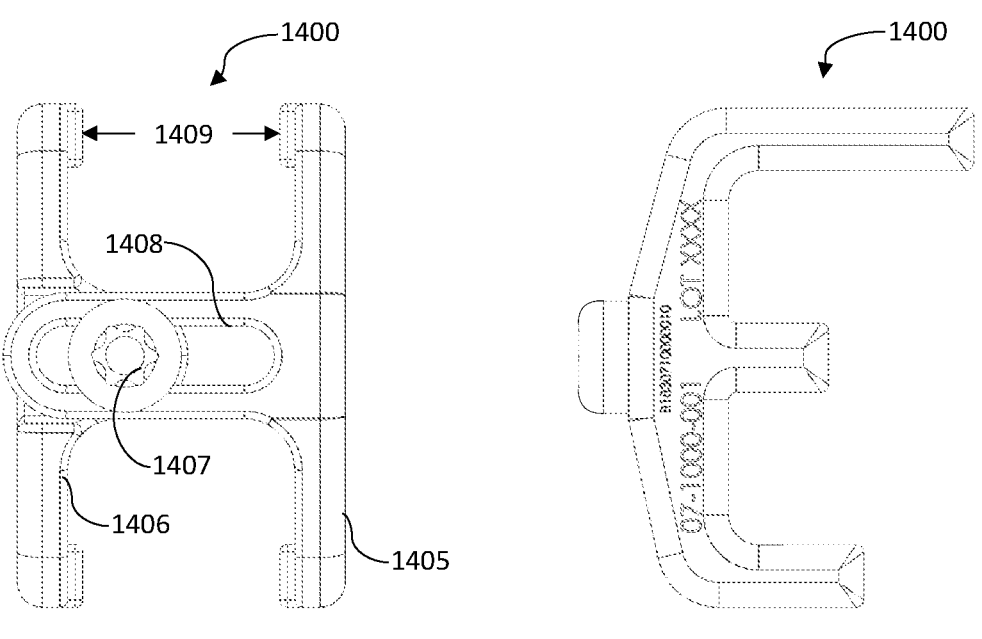
Fig. 14A
Fig. 14B
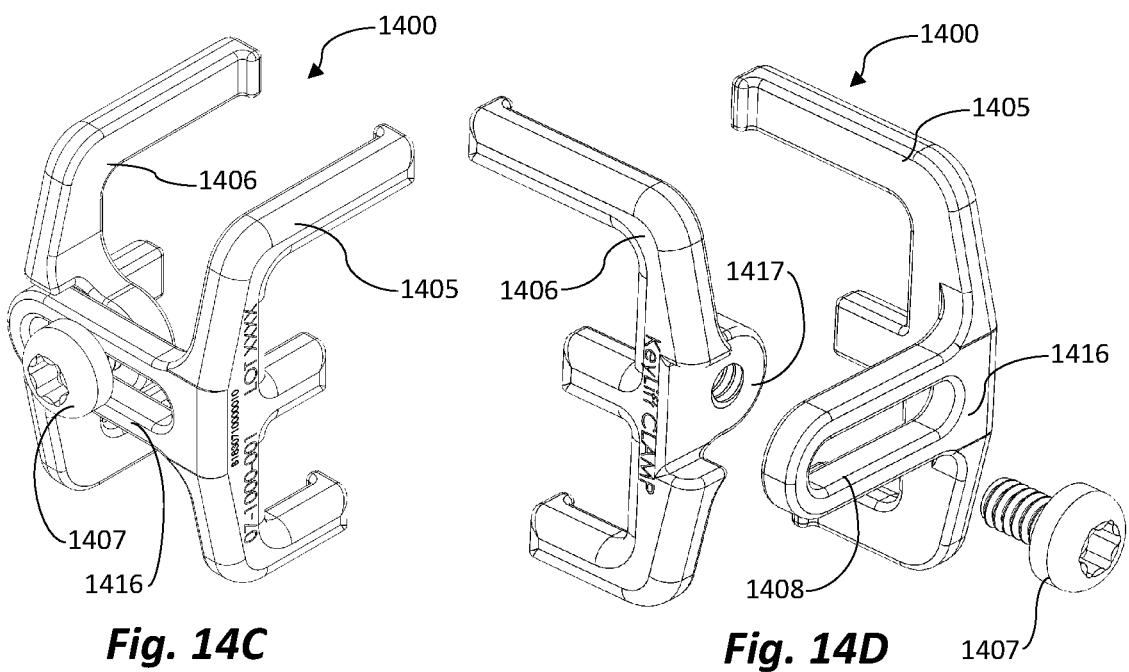
Fig. 14C
Fig. 14D

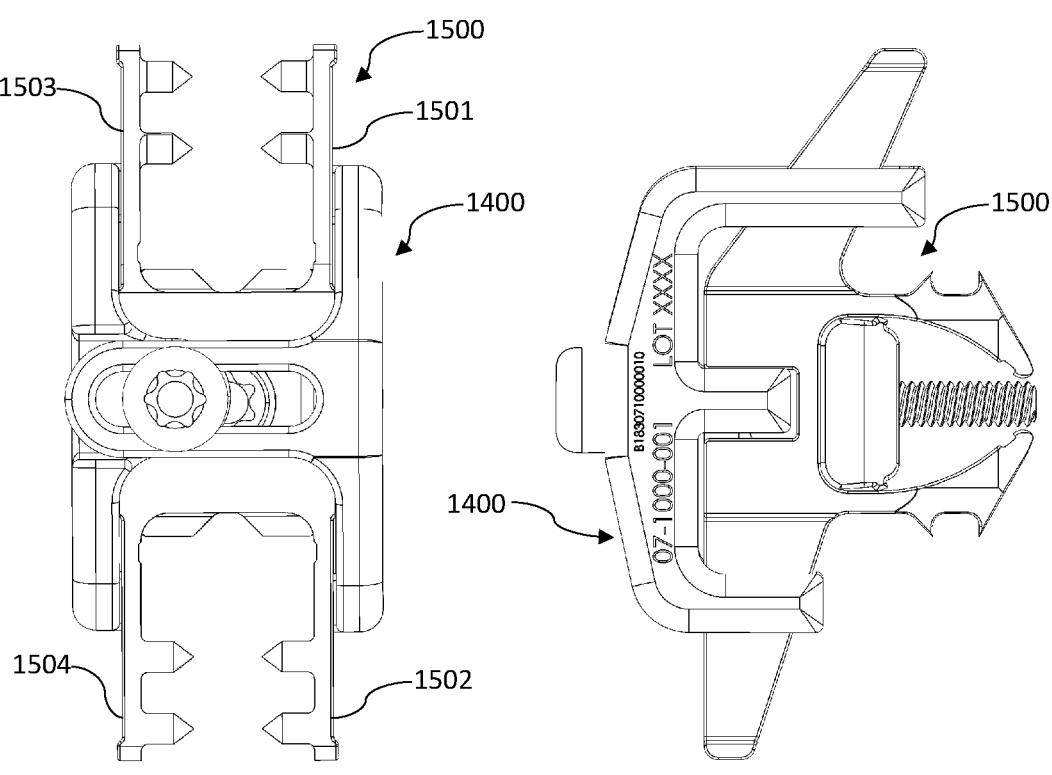
*Fig. 16A*
*Fig. 16B*
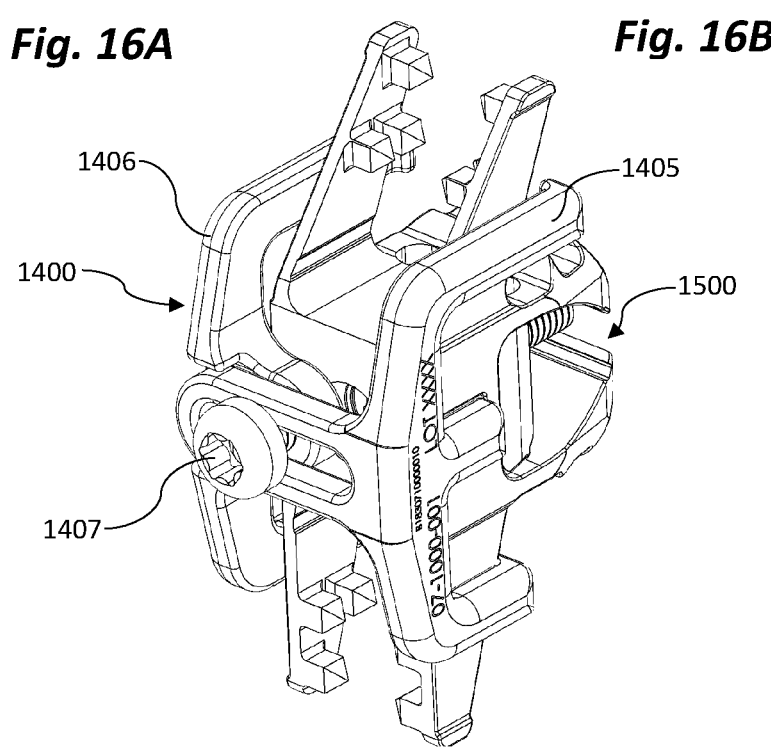
*Fig. 16C*

INTERSPINOUS-INTERLAMINAR STABILIZATION SYSTEMS AND METHODS

CROSS-REFERENCE TO RELATED APPLICATIONS

The present application claims the benefit of U.S. Provisional Patent Application No. 63/445,253, entitled EXPANDABLE INTERSPINOUS-INTERLAMINAR STABILIZATION SYSTEMS AND METHODS, which was filed on Feb. 13, 2023, and is incorporated by reference as though set forth herein in its entirety.

TECHNICAL FIELD

The present disclosure relates generally to surgical systems and methods, and more particularly, to systems and methods for maintaining a desired level of distraction between the spinous processes and laminae of adjacent vertebrae.

BACKGROUND

Various spinal conditions can cause instability in one or more levels of the posterior spine. In particular, narrowing of the spinal canal, known as spinal stenosis and degeneration of the intervertebral disc, can enable the posterior aspects of adjacent vertebrae to come together, which may cause pain or damage by compressing nerve roots or other soft tissues. Various intervertebral and interspinous-interlaminar implants have been developed to limit this compression.

Unfortunately, many known treatments are invasive and/or do not provide an adjustable level of distraction between the affected vertebrae. Some implants are difficult or impossible to apply to multiple adjacent vertebral levels without interfering with each other. There is a need for interspinous-interlaminar stabilization systems and methods that overcome these limitations.

SUMMARY

The various systems and methods of the present disclosure have been developed in response to the present state of the art, and in particular, in response to the problems and needs in the art that have not yet been fully solved by currently available devices and methods for interspinous-interlaminar stabilization systems.

In some embodiments, a system may be configured to maintain spacing between a superior spinous process and a superior lamina, and an inferior spinous process and an inferior lamina, of adjacent vertebrae of a spine. The system may include an implant and a clamp. The implant may include two superior wings that may extend superiorly from a proximal superior surface such that, in an implanted position, the superior spinous process may be engaged between the two superior wings. The implant may also include two inferior wings that may extend inferiorly from a proximal inferior surface such that, in the implanted position, the inferior spinous process may be engaged between the two inferior wings. The clamp may include two superior arms that may be configured to engage the two superior wings to prevent disengagement of the two superior wings from the superior spinous process. The clamp may also include two inferior arms that may be configured to engage the two inferior wings to prevent disengagement of the two inferior wings from the inferior spinous process.

In the system of any preceding paragraph, the clamp may further include a first portion that may be configured to engage a first side of the implant and a second portion that may be configured to engage a second side of the implant, wherein a distance between the first portion and the second portion may be adjustable.

In the system of any preceding paragraph, the clamp may further include a first portion that may be configured to engage a first side of the implant, a second portion that may be configured to engage a second side of the implant, and a fastener that may be configured to securely couple the first portion and the second portion.

In the system of any preceding paragraph, the implant may also include a first lateral aperture and a second lateral aperture. Additionally, the clamp may also include a first locating tab and a second locating tab, wherein the first locating tab may be slidably connectable to the first lateral aperture and the second locating tab may be slidably connectable to the second lateral aperture, thereby limiting translation of the clamp relative to the implant in a superior-inferior direction.

In the system of any preceding paragraph, the clamp may also include a first superior arm comprising a first superior arm tab, a first inferior arm comprising a first inferior arm tab, a second superior arm comprising a second superior arm tab, and a second inferior arm comprising a second inferior arm tab, wherein the first superior arm tab may extend laterally toward the second superior arm, the first inferior arm tab may extend laterally toward the second inferior arm, the second superior arm tab may extend laterally toward the first superior arm, and the second inferior arm tab may extend laterally toward the first inferior arm.

In the system of any preceding paragraph, the first superior arm tab and the second superior arm tab may be configured to engage a pair of superior wings to prevent the first superior arm and the second superior arm from disengaging the pair of superior wings through translation in a proximal direction.

In the system of any preceding paragraph, the first inferior arm tab and the second inferior arm tab may be configured to engage a pair of inferior wings to prevent the first inferior arm and the second inferior arm from disengaging the pair of inferior wings through translation in a proximal direction.

In the system of any preceding paragraph, the two superior arms may be longer than the two inferior arms.

In some embodiments, a system may be configured to maintain spacing between a first bone and a second bone. The system may include an implant that may have a first pair of wings configured to grip a first bone therebetween and a clamp that may be configured to engage the first pair of wings to prevent deflection of the first pair of wings away from the first bone.

In the system of any preceding paragraph, the first pair of wings may be a pair of superior wings, the implant may further have a pair of inferior wings; and the clamp may also include two superior arms that may be configured to engage the pair of superior wings to prevent disengagement of the pair of superior wings from a superior spinous process. The clamp may also include two inferior arms that may be configured to engage the pair of inferior wings to prevent disengagement of the pair of inferior wings from an inferior spinous process.

In the system of any preceding paragraph, the clamp may also include a first superior arm that may include a first superior arm tab, a first inferior arm that may include a first inferior arm tab, a second superior arm that may include a second superior arm tab, and a second inferior arm that may include a second inferior arm tab. Additionally, the first superior arm tab may extend laterally toward the second superior arm, the first inferior arm tab may extend laterally toward the second inferior arm, the second superior arm tab may extend laterally toward the first superior arm, and the second inferior arm tab may extend laterally toward the first inferior arm.

In the system of any preceding paragraph, the first pair of wings may be a pair of superior wings and the first superior arm tab and the second superior arm tab may be configured to engage the pair of superior wings to prevent the first superior arm and the second superior arm from disengaging from the pair of superior wings through translation in a proximal direction.

In the system of any preceding paragraph, the implant may further have a pair of inferior wings and the first inferior arm tab and the second inferior arm tab may be configured to engage the pair of inferior wings to prevent the first inferior arm and the second inferior arm from disengaging from the pair of inferior wings through translation in a proximal direction.

In the system of any preceding paragraph, the clamp may also include a first portion that may be configured to engage a first side of the implant, a second portion that may be configured to engage a second side of the implant, and a fastener that may be configured to securely couple the first portion and the second portion.

In the system of any preceding paragraph, the clamp may also include a first portion that may be configured to engage a first side of the implant and a second portion that may be configured to engage a second side of the implant, wherein a distance between the first portion and the second portion is adjustable.

In some embodiments, a system may be configured to maintain spacing between a superior spinous process and a superior lamina, and an inferior spinous process and an inferior lamina, of adjacent vertebrae of a spine. The system may include an implant that may include, a proximal superior surface comprising a superior concavity shaped to receive the superior spinous process in an implanted position, a proximal inferior surface comprising an inferior concavity shaped to receive the inferior spinous process in the implanted position, a distal superior surface, distal to the proximal superior surface, that faces the superior lamina in the implanted position, a distal inferior surface, distal to the proximal inferior surface, that faces the inferior lamina in the implanted position, a first lateral aperture, and a second lateral aperture. The system may also include a clamp that may have a first locating tab and a second locating tab. Additionally, the first locating tab may be slidably connectable to the first lateral aperture and the second locating tab may be slidably connectable to the second lateral aperture, thereby limiting translation of the clamp relative to the implant in a superior-inferior direction.

In the system of any preceding paragraph, the clamp may also include a first portion that may be configured to engage a first side of the implant and a second portion that may be configured to engage a second side of the implant, wherein a distance between the first portion and the second portion may be adjustable.

In the system of any preceding paragraph, the clamp may also include a first portion that may be configured to engage a first side of the implant, a second portion that may be configured to engage a second side of the implant, and a fastener that may be configured to securely couple the first portion and the second portion.

In the system of any preceding paragraph, the implant may include a pair of superior wings and a pair of inferior wings. Additionally, the clamp may include two superior arms that may be configured to engage the pair of superior wings to prevent disengagement of the pair of superior wings from a superior spinous process and two inferior arms that may be configured to engage the pair of inferior wings to prevent disengagement of the pair of inferior wings from an inferior spinous process.

In the system of any preceding paragraph, the clamp may be configured to engage the implant comprising one or more pairs of wings, wherein the clamp may be configured to prevent deflection of the one or more pairs of wings away from a portion of bone.

In some embodiments, a method for implanting an implant in a space between a superior spinous process and a superior lamina, and an inferior spinous process and an inferior lamina of adjacent vertebrae of a spine may include inserting the implant into the space, wherein the implant may include two superior wings extending superiorly from a proximal superior surface and two inferior wings extending inferiorly from a proximal superior surface. The method of Inserting the implant into the space may include, causing the superior spinous process to be received between the two superior wings and causing the inferior spinous process to be received between the two inferior wings. The method may also include, locating a clamp onto the implant, wherein the clamp may include, two superior arms that may be configured to engage the two superior wings to prevent disengagement of the two superior wings from the superior spinous process and two inferior arms that may be configured to engage the two inferior wings to prevent disengagement of the two inferior wings from the inferior spinous process. The method may further include, adjusting a distance between a first and second portions of the clamp to engage the implant, and securing the distance between the first and second portions of the clamp using a fastener.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

FIGS. 2A, 2B, 2C, and 2D are perspective, side elevation, plan, and rear elevation views of the implant of FIGS. 1A, 1B, 1C, and 1D, in a deployed configuration.

FIGS. 14A, 14B, 14C and 14D are front, side, perspective, and exploded perspective views of an interspinous-interlaminar implant clamp according to 8 another embodiment of the present disclosure.

FIGS. 16A, 16B and 16C are front, side, and perspective views of an interspinous-interlaminar implant and interspinous-interlaminar implant clamp assembly according to one embodiment of the present disclosure, in a retracted configuration.

DETAILED DESCRIPTION

Figures 1A, 1B, 1C, 1D:
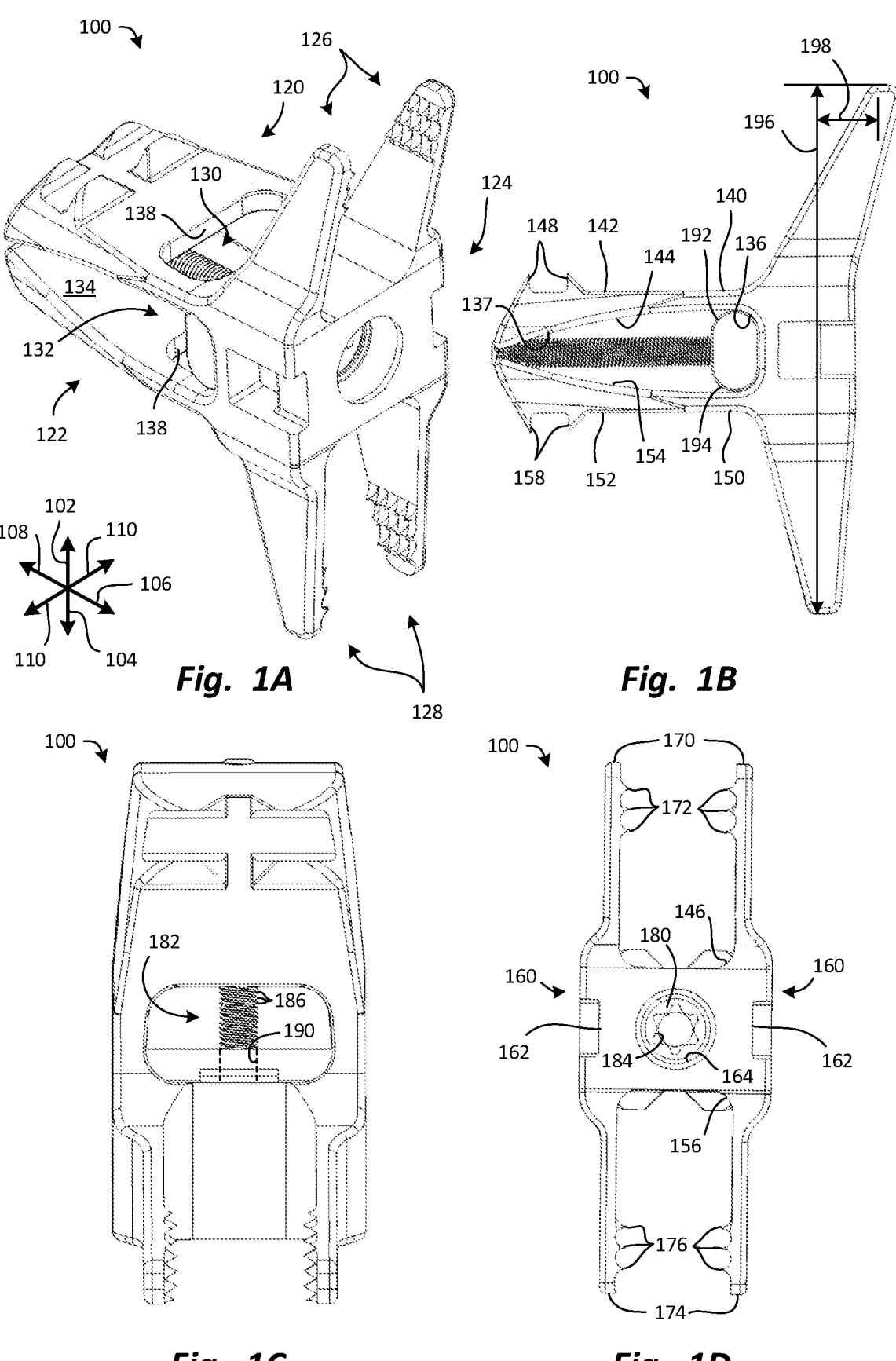
FIGS. 1A, 1B, 1C, and 1D are perspective, side elevation, plan, and rear elevation views of an interspinous-interlaminar implant according to one embodiment of the present disclosure, in a retracted configuration.

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1A through 12B, is not intended to limit the scope of the claims, but is merely representative exemplary of exemplary embodiments of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The system and method of use in accordance with the present application may overcome one or more of the above-discussed problems commonly associated with conventional interspinous stabilization systems and methods. Specifically, interspinous and interlaminar stabilization systems and methods presented herein may enable interspinous process-interlaminar implants to be reliably placed with smaller incisions, less intrusive implants, and shortened recovery times. These and other unique features of the system and method of use are discussed below and illustrated in the accompanying drawings.

FIGS. 1A, 1B, 1C, and 1D are perspective, side elevation, plan, and rear elevation views of an interspinous-interlaminar implant, or implant 100, according to one embodiment of the present disclosure, in a retracted configuration. The implant 100 may be used to stabilize the range of motion of a superior vertebra 80 relative to an inferior vertebra 82 (shown in FIGS. 5A and 5B). The superior vertebra 80 may have a superior spinous process 90 and a superior lamina 94, and the inferior vertebra 82 may have an inferior spinous process 92 and an inferior lamina 96. The implant 100 may be implanted between the superior spinous process 90 and the superior lamina 94, and the inferior spinous process 92 and the inferior lamina 96 to distract the inferior spinous process 92 and the inferior lamina 96 relative to the superior spinous process 90 and the superior lamina 94, thereby limiting posterior compression of nerves and/or other soft tissues between the posterior aspects of the superior vertebra 80 and the inferior vertebra 82. The superior spinous process 90 and the superior lamina 94 may be collectively referred to as the superior spinous process-lamina, and the inferior spinous process 92 and the inferior lamina 96 may be collectively referred to as the inferior spinous process-lamina.

Various directions will be referenced in the present disclosure. These are illustrated in FIG. 1A, and include a superior direction 102, an inferior direction 104, a proximal direction 106, a distal direction 108, and two lateral directions 110 (oriented opposite to each other). The superior direction 102 and the inferior direction 104 may, combined, define a superior-inferior direction. The proximal direction 106 and the distal direction 108 may, combined, define a proximal-distal direction. These directions are only shown in FIG. 1A, but apply to all figures and embodiments set forth herein.

As shown, the implant 100 may have a superior member 120, an inferior member 122, and an interconnecting member 124 that couples the superior member 120 to the inferior member 122. The superior member 120 and the inferior member 122 may each be oriented generally along the proximal-distal direction. The superior member 120, the inferior member 122, and the interconnecting member 124 may optionally be formed as a single piece with each other. In alternative embodiments, these members may be formed separately and coupled together through the use of any attachment methods known in the art.

The implant 100 may also have two superior wings 126 extending generally along the superior direction 102 from the superior member 120, and two inferior wings 128 extending generally along the inferior direction 104 from the inferior member 122. When the implant 100 is in an implanted position between the superior spinous process 90 and the superior lamina 94, and the inferior spinous process 92 and the inferior lamina 96, the superior spinous process 90 may be engaged between the superior wings 126, and the inferior spinous process 92 may be engaged between the inferior wings 128. The superior wings 126 and the inferior wings 128 may help keep the implant 100 in place in the space between the superior spinous process 90 and the superior lamina 94, and the inferior spinous process 92 and the inferior lamina 96, particularly when the superior vertebra 80 and the inferior vertebra 82 move such that the superior spinous process 90 and the inferior spinous process 92 are drawn apart from each other. The superior wings 126 and the inferior wings 128 may also help further stabilize the superior vertebra 80 relative to the inferior vertebra 82 by lateral motion of the inferior vertebra 82 relative to the superior vertebra 80. However, the superior wings 126 and the inferior wings 128 are optional, and may be omitted in alternative embodiments, as will be discussed subsequently.

The implant 100 may further have a threaded member 130 extending generally along the proximal-distal direction. The threaded member 130 may be operable to move a threaded block 132 distally to move the implant 100 from a retracted configuration to a deployed configuration. In the retracted configuration, shown in FIGS. 1A, 1B, 1C, and 1D, the implant 100 is relatively compact in the superior-inferior direction, and fits relatively easily into the space between the superior spinous process 90 and the superior lamina 94, and the inferior spinous process 92 and the inferior lamina 96. Conversely, in the deployed configuration shown in FIGS. 2A, 2B, 2C, and 2D, the distal end of the implant 100 is relatively larger in the superior-inferior direction, causing the superior member 120 and the inferior member 122 to contact and engage the superior spinous process 90 and/or the superior lamina 94 and the inferior spinous process 92 and/or the inferior lamina 96, respectively to restrain motion of the superior spinous process-lamina and the inferior spinous process-lamina toward each other.

The threaded block 132 may move along the proximal-distal direction within a cavity 134 defined between the superior member 120 and the inferior member 122. More specifically, the cavity 134 may have a proximal end 136 and a distal end 137. When the threaded block 132 is in or near the proximal end 136, the implant 100 may be in the retracted configuration. Conversely, when the threaded block 132 is in or near the distal end 137, the implant 100 may be in the deployed configuration. As the threaded block 132 moves towards the distal end, the superior member 120 and inferior member 122 may incrementally deform and deploy, as will be discussed in greater detail subsequently.

The superior member 120 and the inferior member 122 may have windows 138 that provide access to the cavity 134 from superior to the superior member 120, and from inferior to the inferior member 122, respectively. Thus, the windows 138 may receive bony protrusions of the superior spinous process 90, the superior lamina 94, the inferior spinous process 92, and/or the inferior lamina 96 to further secure the implant 100 relative to the superior spinous process-lamina and the inferior spinous process-lamina. Additionally, or alternatively, the windows 138 may facilitate osseointegration between the superior spinous process-lamina and the inferior spinous process-lamina. In some embodiments, bone graft or other biologics may be inserted into the cavity 134 before or after implantation of the implant 100 to encourage a column of bone to grow between the superior spinous process-lamina and the inferior spinous process-lamina, through the windows 138 and the cavity 134.

The superior member 120 and the inferior member 122 may each be functionally divided into proximal and distal ends. As embodied in FIGS. 1A, 1B, 1C, and 1D, the proximal and distal ends of the superior member 120 may be formed as a single piece with each other, and the proximal and distal ends of the inferior member 122 may similarly be formed as a single piece with each other. However, in alternative embodiments, a superior member and/or an inferior member may have separately-formed and subsequently coupled proximal and distal portions.

The superior member 120 may have a proximal superior surface 140 and a distal superior surface 142, both of which face toward the superior spinous process 90 and the superior lamina 94. The superior member 120 may also have an interior superior surface 144 that forms the superior boundary of the cavity 134 and faces toward the threaded member 130 and the threaded block 132. The proximal superior surface 140 may have a superior concavity 146 with a concave shape that receives a portion of the superior spinous process 90. The distal superior surface 142 may have superior ridges 148 that extend generally laterally to contact the superior spinous process 90 and/or the superior lamina 94 upon deployment of the implant 100. The superior ridges 148 may have generally sharpened shapes that allow the superior ridges 148 to penetrate the cortical exterior of the superior spinous process 90 and/or the superior lamina 94 to secure the distal superior surface 142 relative to the superior spinous process 90 and the superior lamina 94 upon deployment of the implant 100. In some embodiments, the superior ridges 148 may be positioned to contact only the superior lamina 94.

Similarly, the inferior member 122 may have a proximal inferior surface 150 and a distal inferior surface 152, both of which face toward the inferior spinous process 92 and the inferior lamina 96. The inferior member 122 may also have an interior inferior surface 154 that forms the inferior boundary of the cavity 134 and faces toward the threaded member 130 and the threaded block 132. The proximal inferior surface 150 may have an inferior concavity 156 with a concave shape that receives a portion of the inferior spinous process 92. The distal inferior surface 152 may have inferior ridges 158 that extend generally laterally to contact the inferior spinous process 92 and/or the inferior lamina 96 upon deployment of the implant 100. The inferior ridges 158 may have generally sharpened shapes that allow the inferior ridges 158 to penetrate the cortical exterior of the inferior spinous process 92 and/or the inferior lamina 96 to secure the distal inferior surface 152 relative to the inferior spinous process 92 and the inferior lamina 96 upon deployment of the implant 100.

The interconnecting member 124 may have a pair of laterally-facing surfaces 160 facing in the lateral directions 110. The laterally-facing surfaces 160 may each have a lateral aperture 162 that extend into the interconnecting member 124 to define an inserter interface that facilitates coupling of the implant 100 to an inserter 400, as will be shown and described in connection with FIG. 4. The interconnecting member 124 may also have a rear aperture 164 that provides access, from a proximal direction, to the threaded member 130 so that the threaded member 130 can be rotated by a user via the inserter 400 to move the implant 100 between the retracted and deployed configurations.

The superior wings 126 may have superior tips 170 that represent the furthest superior extents of the superior wings 126. The superior wings 126 may also have superior teeth 172, which may be positioned proximate the superior tips 170, and protrude inwardly to grip the superior spinous process 90 when the superior spinous process 90 is received between the superior wings 126. The superior teeth 172 may penetrate the cortical exterior of the superior spinous process 90 to secure the superior wings 126 relative to the superior spinous process 90, thereby preventing relative motion between the superior spinous process 90 and the implant 100.

Similarly, the inferior wings 128 may have inferior tips 174 that represent the furthest inferior extents of the inferior wings 128. The inferior wings 128 may also have inferior teeth 176, which may be positioned proximate the inferior tips 174, and protrude inwardly to grip the inferior spinous process 92 when the inferior spinous process 92 is received between the inferior wings 128. The inferior teeth 176 may penetrate the cortical exterior of the inferior spinous process 92 to secure the inferior wings 128 relative to the inferior spinous process 92, thereby preventing relative motion between the inferior spinous process 92 and the implant 100.

Advantageously, the superior tips 170 may be displaced, along the proximal-distal direction, from the inferior tips 174. As shown, the inferior tips 174 may be separated from the superior tips 170 by a superior-inferior displacement 196, and by a proximal-distal displacement 198. The proximal-distal displacement 198 may be sufficient to provide some flexibility whereby the implant 100 can be implanted in the orientation shown in FIG. 1A, or reversed so that the superior wings 126 grip the inferior spinous process 92 and the inferior wings 128 grip the superior spinous process 90. Notably, use of the terms "superior" and "inferior" in relation to the implants described herein does not imply any required orientation upon implantation.

The threaded member 130 may have a head 180 and a shank 182. The head 180 may have an enlarged shape relative to the shank 182. The shank 182 may extend along the proximal-distal direction, as shown in FIGS. 1A, 1B, 1C, and 1D. As further shown, the head 180 may have a socket 184 shaped to receive a corresponding drive feature of the inserter 400. As shown, the socket 184 may have a star shape or the like; this shape may match that of the drive feature so that the drive feature can impart torque to the threaded member 130 to rotate the threaded member 130 relative to the superior member 120 and the inferior member 122. In alternative embodiments, the socket 184 may have a different shape, or may be replaced by one or more positive features such as a boss that cooperate any drive feature shape known in the art.

The shank 182 may have threads 186 with a helical shape that can, upon rotation of the threaded member 130, drive the threaded block 132 to move between the proximal end 136 and the distal end 137 of the cavity 134. A proximal portion of the shank 182 (not shown) may have a smooth portion that passes through the rear aperture 164 of the interconnecting member 124 so that the threaded member 130 is rotatably retained relative to the interconnecting member 124.

The threaded block 132 may have a hole 190, a superior surface 192, and an inferior surface 194. The hole 190 may have threads that receive the threads 186 of the shank 182 of the threaded member 130 such that the threaded member 130 may rotate in place relative to the interconnecting member 124 while driving linear motion of the threaded block 132. The superior surface 192 may engage the interior superior surface 144 of the superior member 120, and the inferior surface 194 may engage the interior inferior surface 154 of the inferior member 122. A snap ring (not visible) or other structure may be used to retain the threaded member 130 relative to the interconnecting member 124.

As shown, the cavity 134 may be shaped such that the proximal end 136 of the cavity 134 is wider, along the superior/inferior direction, than the distal end 137 of the cavity 134. Thus, as the threaded block 132 is driven from the proximal end 136 toward the distal end 137, the superior surface 192 may press against the interior superior surface 144 and the inferior surface 194 may press against the interior inferior surface 154 to widen the distal end 137 of the cavity 134. This may cause the distal portions of the superior member 120 and the inferior member 122 to move apart from each other, thus causing the distal superior surface 142 and the distal inferior surface 152 to move away from each other and toward the superior spinous process-lamina and the inferior spinous process-lamina, respectively. The resulting deployed configuration is shown in FIGS. 2A, 2B, 2C, and 2D.

FIGS. 2A, 2B, 2C, and 2D are perspective, side elevation, plan, and rear elevation views of the implant 100 of FIGS. 1A, 1B, 1C, and 1D, in the deployed configuration. As shown, the threaded block 132 has been driven to reside in the distal end 137 of the cavity 134, and the distal superior surface 142 and the distal inferior surface 152 have been spread apart.

The implant 100 may be formed of any known biocompatible materials, including but not limited to biocompatible metals such as Titanium and Titanium alloys, shape memory alloys such as Nitinol, biocompatible ceramics, and biocompatible polymers such as Polyether ether ketone (PEEK). In some embodiments, the implant 100 may be formed of a less rigid material so that the superior member 120 and the inferior member 122 can bend to spread apart from each other in order to allow the distal end 137 of the cavity 134 to widen as the threaded block 132 moves into the distal end 137.

Further, in some embodiments, the superior member 120 and the inferior member 122 may be made relatively thin so that they can bend between the proximal superior surface 140 and the distal superior surface 142, and between the proximal inferior surface 150 and the distal inferior surface 152. Thus, the superior member 120 may define a superior living hinge 200, and the inferior member 122 may define an inferior living hinge 202. The superior living hinge 200 and the inferior living hinge 202 may enable the distal portions of the superior member 120 and the inferior member 122 to flex outward as the implant 100 moves to the deployed configuration.

Various instruments may be used to facilitate implantation of the implant 100. Some of these will be shown and described in connection with FIGS. 3A, 3B, and 4. Those of skill in the art will recognize that a wide variety of instruments may be used in connection with the implants disclosed herein, including any instruments known in the art of implanting interspinous process and/or interlaminar devices. Likewise, any surgical methods may be used in connection with the implants disclosed herein, including any surgical methods known in the art of implanting interspinous process and/or interlaminar devices.

Figure 3A:
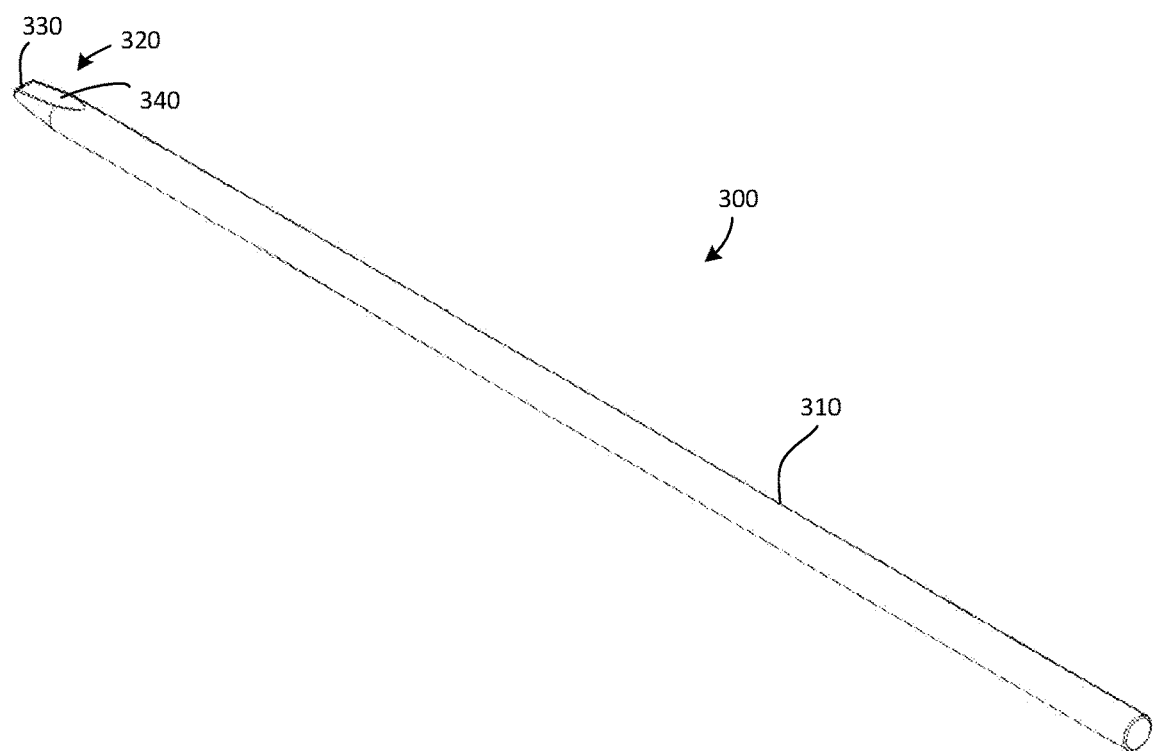
FIGS. 3A and 3B are perspective views of a probe and a rasp trial suitable for preparing a space between adjacent spinous processes and laminae for implantation of the implant of FIGS. 1A, 1B, 1C, and 1D, according to one embodiment of the present disclosure.
Figure 3B:
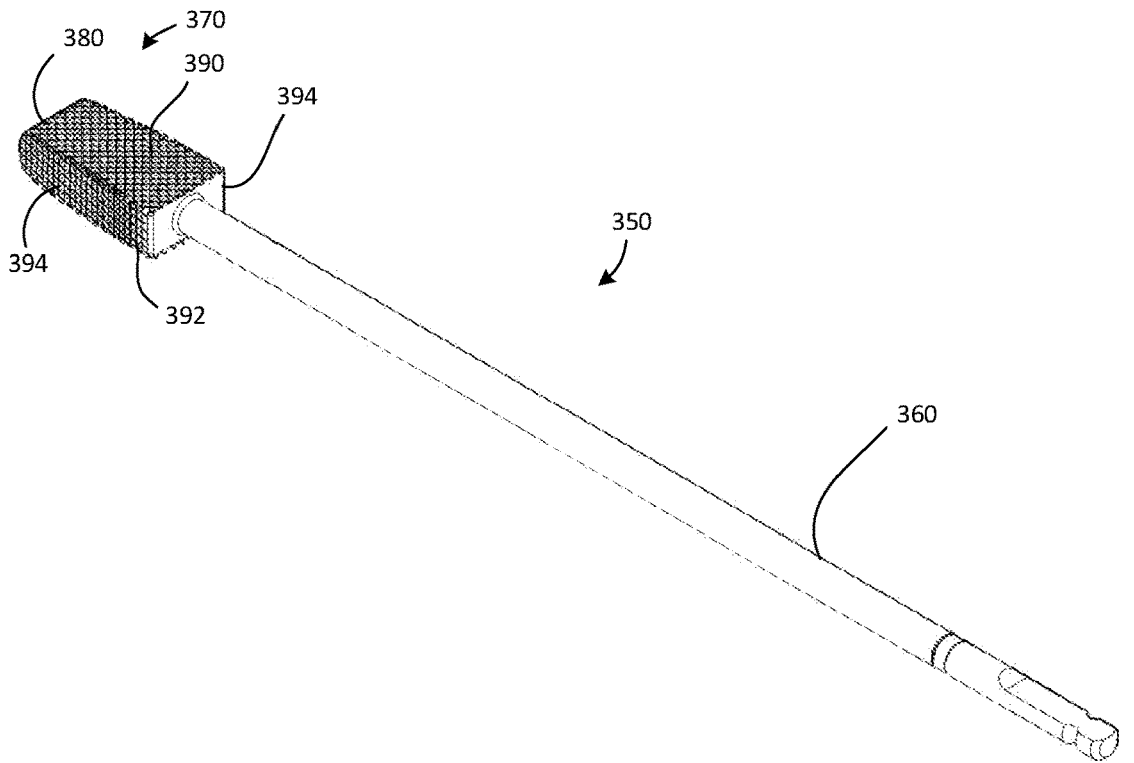

FIGS. 3A and 3B are perspective views of a probe 300 and a rasp trial 350 suitable for preparing a space between adjacent spinous processes and laminae for implantation of the implant 100 of FIGS. 1A, 1B, 1C, and 1D, according to one embodiment of the present disclosure. The probe 300 may be used to explore the space between the superior spinous process 90 and the superior lamina 94, and the inferior spinous process 92 and the inferior lamina 96, for example, to test for the location of nerves and/or other sensitive tissues. The rasp trial 350 may be used to abrade away excess bone from the adjoining surfaces of the superior spinous process 90, the superior lamina 94, the inferior spinous process 92, and/or the inferior lamina 96 and/or test for proper fit of the implant 100.

More particularly, the probe 300 may have a shaft 310 and a head 320. The shaft 310 may be held by the surgeon, either directly or via another instrument. The head 320 may be inserted into the space between the superior spinous process 90 and the superior lamina 94, and the inferior spinous process 92 and the inferior lamina 96. The head 320 may have a blunt tip 330 shaped to facilitate exploration of the space between the superior spinous process-lamina and the inferior spinous process-lamina, while avoiding damage to adjacent soft tissues. The head 320 may further have beveled surfaces 340 that cause the head 320 to have a relatively larger proximal end than its distal end. The beveled surfaces 340 may facilitate insertion of the blunt tip 330 into soft tissues within the space between the superior spinous process-lamina and the inferior spinous process-lamina.

The rasp trial 350 may have a shaft 360 and a head 370. Like the shaft 310 of the probe 300, the shaft 360 may also be held by the surgeon, either directly or with the aid of another instrument. The head 370 may have a blunt tip 380 that also avoids damage to tissues distal to the head 370, which may include nerve tissues such as the spinal column and nerve roots. The head 370 may also have a superior surface 390, an inferior surface 392, and lateral surfaces 394 that are all roughened to permit the head 370 to abrade away surrounding tissues, such as the adjoining surfaces of the superior spinous process-lamina and the inferior spinous process-lamina, in response to reciprocating motion of the head 370 within the space between the superior spinous process-lamina and the inferior spinous process-lamina.

In addition to preparing the space between the superior spinous process 90 and the superior lamina 94, and the inferior spinous process 92 and the inferior lamina 96, the rasp trial 350 may also be used to assess the fit of the implant 100 within the space between the superior spinous process-lamina and the inferior spinous process-lamina. For example, the superior surface 390 may generally mimic the size and shape of the superior aspect of the superior member 120, including the proximal superior surface 140 and the distal superior surface 142. Similarly, the inferior surface 392 may generally mimic the size and shape of the inferior aspect of the inferior member 122, including the proximal inferior surface 150 and the distal inferior surface 152. The lateral surfaces 394 may mimic the lateral aspects of the implant 100, including the laterally-facing surfaces 160 of the interconnecting member 124, and the lateral aspects of the superior member 120 and the inferior member 122, combined.

Thus, insertion of the head 370 into the space between the superior spinous process-lamina and the inferior spinous process-lamina may help the surgeon assess whether the implant 100 will fit properly within the space. A kit of implants (not shown) may include implants similar in configuration to the implant 100, but different in size and/or shape, in order to accommodate various bone morphologies. Likewise, the kit may include multiple different rasp trials, each having a size and shape that matches one of the implants of the kit, so that each rasp trial can be used as a trial for one of the implants.

Figure 4:
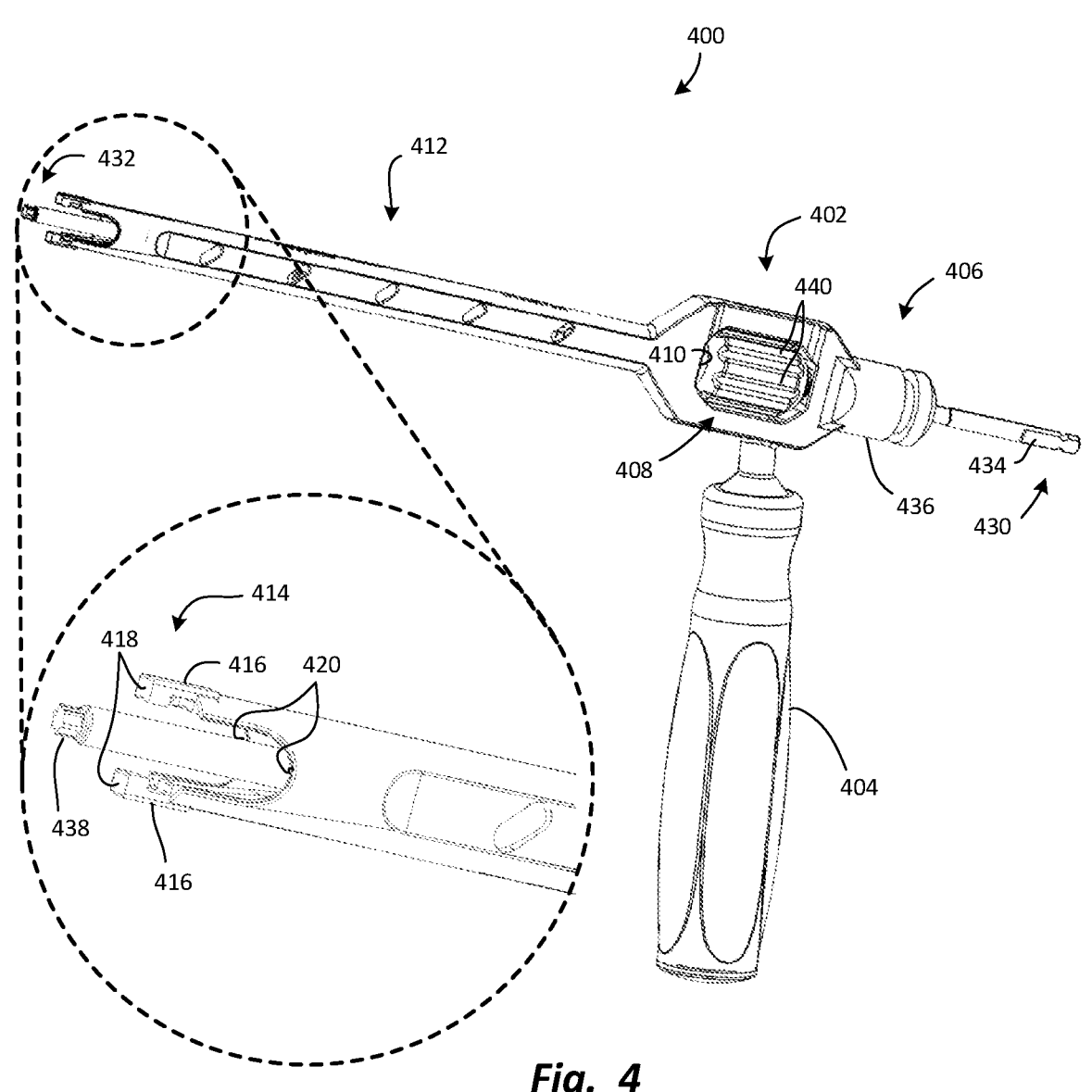
FIG. 4 is a perspective view of an inserter configured to place the implant of FIGS. 1A, 1B, 1C, and 1D, according to one embodiment of the present disclosure.

FIG. 4 is a perspective view of an inserter 400 configured to place the implant 100 of FIGS. 1A, 1B, 1C, and 1D, according to one embodiment of the present disclosure. The inserter 400 may also be used to rotate the threaded member 130 to move the implant 100 from the retracted configuration to the deployed configuration.

The inserter 400 may have a body 402, a handle 404, a drive rod 406, and an advancement knob 408. The implant 100 may be coupled to the body 402, and the handle 404 may be gripped by hand to position the implant 100 in the space between the superior spinous process-lamina and the inferior spinous process-lamina. The drive rod 406 may be a rotary element that rotates the threaded member 130, and the advancement knob 408 may selectively advance or retract the drive rod 406.

The body 402 may have a proximal window 410, a shaft 412, and a coupling interface 414. The proximal window 410 may contain the advancement knob 408 such that the advancement knob 408 can be manually rotated by a surgeon. The shaft 412 may extend between the proximal window 410 and the coupling interface 414, which may be positioned at the distal end of the shaft 412.

The coupling interface 414 may have two arms 416 that have bosses 418 that protrude inward. The arms 416 may be spaced apart such that the interconnecting member 124 of the implant 100 can be inserted between the arms 416, with the arms 416 on either lateral side of the interconnecting member 124. The bosses 418 may be sized to be received within the lateral apertures 162 on the laterally-facing surfaces 160 of the interconnecting member 124.

The coupling interface 414 may be configured such that the arms 416 can be flexed apart to permit the bosses 418 to enter and/or exit the lateral apertures 162. Specifically, the shaft 412 may have recesses 420 that permit the arms 416 to flex apart. Thus, the implant 100 may be coupled to the coupling interface 414 by spreading the arms 416 such that the bosses 418 can be inserted into the lateral apertures 162. Likewise, the implant 100 may be decoupled from the coupling interface 414 by again spreading the arms 416 to remove the bosses 418 from the lateral apertures 162.

The drive rod 406 may have a proximal end 430 and a distal end 432. The proximal end 430 may have a proximal flat 434 that can interface with a rotating tool, such as a hand crank or surgical drill. The distal end 432 may have a drive feature 436 that can be coupled to the threaded member 130, for example, by inserting the drive feature 436 into the socket 184 of the head 180 of the threaded member 130. The drive rod 406 may also have a drive knob 438 positioned near the proximal end 430 such that the drive knob 438 can be rotated by hand to rotate the drive rod 406. Thus, the drive rod 406 may be rotated with the proximal flat 434 or the drive knob 438, either with a tool or by hand, to rotate the threaded member 130 to move the implant 100 between retracted and deployed configurations.

With the implant 100 coupled to the coupling interface 414 of the inserter 400, the advancement knob 408 may be used to advance the drive feature 436 into the socket 184, or withdraw the drive feature 436 from the socket 184. Thus, the drive rod 406 may be disengaged from the implant 100 when the implant 100 has reached the desired level of deployment, without decoupling the inserter 400 from the implant 100. The advancement knob 408 may optionally have ridges 440, knurling, or other surface features that facilitate manual gripping and rotation of the advancement knob 408.

Various surgical methods may be used to place the implant 100. In some embodiments, the surgical method may include (1) preparation, (2) microsurgical decompression, (3) implant site preparation, (4) implant insertion, and (5) wound closure.

Preparation may include placing the patient in the prone position on a surgical frame, avoiding hyperlordosis of the spinal segment(s) to be operated upon. A neutral position or a slight kyphosis may be advantageous for surgical decompression and/or appropriate interspinous distraction. A midline incision may be performed. The muscle may be sharply dissected lateral to the supraspinous ligament, preserving the entire thickness of the supraspinous ligament. Alternatively, the supraspinous ligament may be resected, depending on a surgeon's preference. In such a case, the interspinous ligament may be sacrificed and any bony overgrowth of the spinous process that may interfere with insertion may also resected.

Paraspinal muscles may be stripped off the laminae while preserving the facet capsules. Dependent on the pathology, a microsurgical unilateral decompression may be performed and then the supraspinous ligament together with the fascia and muscle from the opposite side may be mobilized together. The supraspinous ligament may be dissected subperiostally and preserved as a thick cuff and retracted laterally. If possible, a small portion of the bony tip may be resected together with the supraspinous ligament. This may provide for faster healing after reconstruction of the ligament.

Microsurgical decompression may be commenced by resecting the ligamentum flavum. The decompression may then be performed, relieving all points of neural compression. The implant site may be prepared by utilizing trials to define appropriate implant size.

Implant site preparation may be commenced by placing the trial instrument (for example, the rasp trial 350) to evaluate proper contact with the spinous process and the desired amount of interspinous distraction. The rasp trial 350 may then be used to remove bone to prepare the area for the implant 100. Some bony resection of the spinous process may be needed to ensure proper contact of the implant 100 with the superior spinous process-lamina and the inferior spinous process-lamina. To ensure the implant 100 is inserted to the proper depth, a small portion of the laminar surface may also be partially resurfaced. Distraction may be appropriate to prevent any settling of the interspinous distance after successful decompression of the spinal stenosis.

Insertion of the implant 100 may be commenced by slightly spreading the superior wings 126 and/or the inferior wings 128 with pliers or another tool, at the mid-portion of each of the superior wings 126 and/or the inferior wings 128, to ensure the appropriate depth of insertion. The implant 100 may be introduced via impaction utilizing a mallet, for example, by striking the proximal end of the inserter 400 with the implant 100 coupled to the inserter 400. In some embodiments, a handle (not shown) may be secured to the proximal end 430 to facilitate impaction.

The implant 100 may then be expanded by rotating the drive rod 406 clockwise until a tactile click are felt. Proper depth may be determined if a beaded tip probe can be passed freely, leaving a 3-4 mm separation from the dura. If the implant 100 is not seated appropriately, further resurfacing or slightly more impaction force may be utilized. If the superior wings 126 and/or the inferior wings 128 do not have sufficient bony contact, additional stability may be achieved by slightly crimping the superior wings 126 and/or the inferior wings 128, as appropriate.

Wound closure may be commenced by re-suturing the supraspinous ligament. A "figure 8" suture or the like may be placed through two bone holes in the spinous process and through the supraspinous ligament. Alternatively, the fascia and the supraspinous ligament may be closed in one layer over the spinous processes. A surgical drain may be placed per surgeon preference. Paraspinal muscles may be reattached to the supraspinous ligament. Skin may be closed in the usual manner.

Figure 5A:
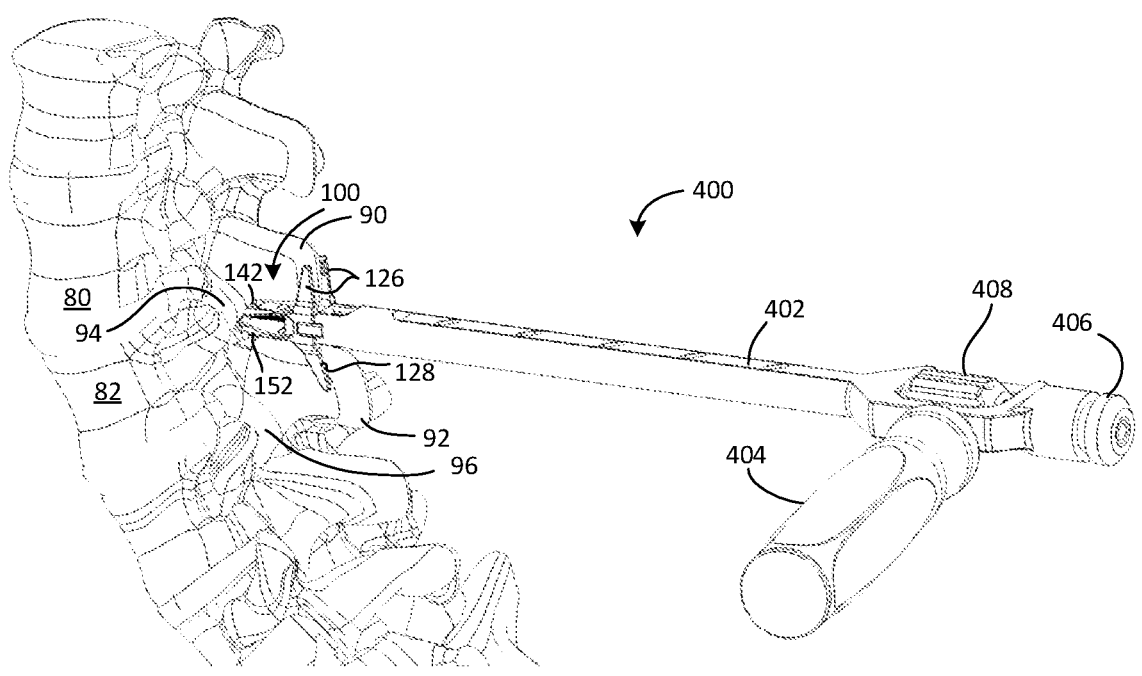
FIGS. 5A and 5B are perspective views of the implant of FIGS. 1A, 1B, 1C, and 1D implanted in the space between adjacent spinous processes and laminae, in a retracted configuration and a deployed configuration, respectively, according to one embodiment of the present disclosure.
Figure 5B:
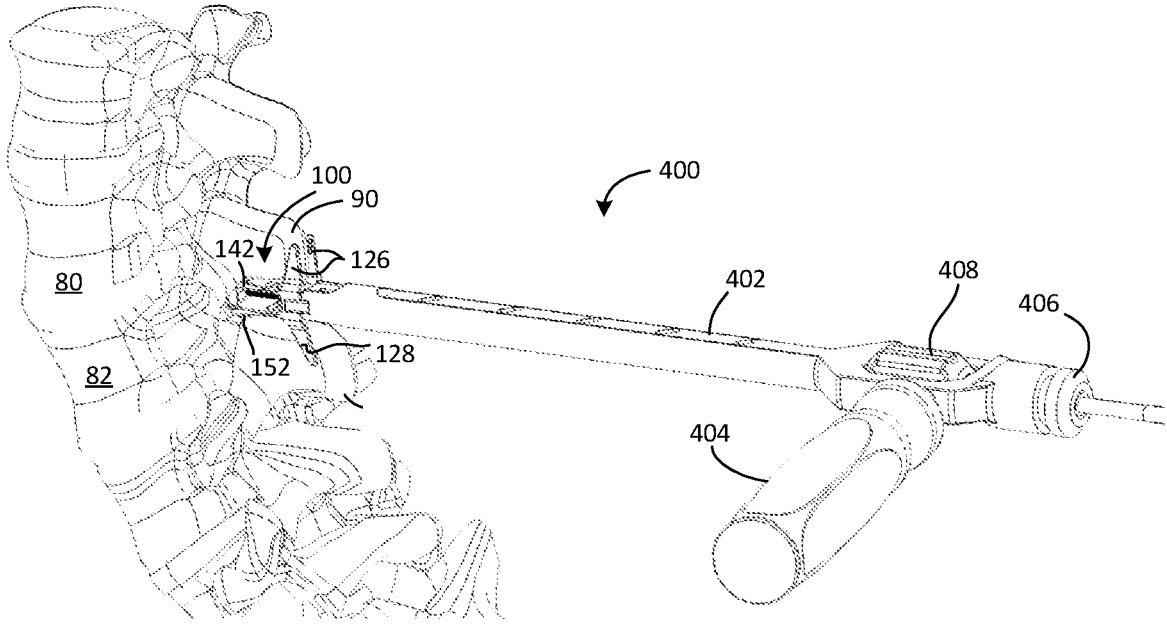

FIGS. 5A and 5B are perspective views of the implant 100 of FIGS. 1A, 1B, 1C, and 1D implanted in the space between adjacent spinous process-laminae, in a retracted configuration and a deployed configuration, respectively, according to one embodiment of the present disclosure. In FIG. 5A, the implant 100 is retracted to facilitate insertion. The distal superior surface 142 and the distal inferior surface 152 have not yet been spread apart. In FIG. 5B, the implant 100 has been moved to the deployed configuration to move the distal superior surface 142 and the distal inferior surface 152 into contact with the superior spinous process-lamina and the inferior spinous process-lamina.

Notably, deployment of the implant 100 is optional. In some procedures, the distal superior surface 142 and the distal inferior surface 152 may already be in sufficient contact with the superior spinous process-lamina and the inferior spinous process-lamina after insertion of the implant 100 into the interspinous process-interlaminar space. Thus, deployment of the implant 100 may not be needed.

Further, in some procedures, the implant 100 may be only partially deployed. For example, the distal superior surface 142 and the distal inferior surface 152 may not be in sufficient contact with the superior spinous process-lamina and/or the inferior spinous process-lamina upon insertion of the implant 100 into the interspinous-intralaminar space, but may come into sufficient contact after only partial deployment of the implant 100. The threaded member 130 may only be rotated sufficiently to move the threaded block 132 to a position between the proximal end 136 and the distal end 137 of the cavity 134. The distal superior surface 142 and the distal inferior surface 152 may move apart, but not to the extent of their full range of motion.

If desired, the interior superior surface 144 and the interior inferior surface 154 may be shaped to provide generally continuous spreading of the distal superior surface 142 and the distal inferior surface 152 as the threaded member 130 is rotated. The shapes of the interior superior surface 144 and the interior inferior surface 154 may be selected such that the displacement between the distal superior surface 142 and the distal inferior surface 152 varies in linear relationship to rotation of the threaded member 130. Thus, the motion of the distal superior surface 142 and the distal inferior surface 152 may be relatively gradual and predictable, allowing the surgeon to determine the appropriate degree of deployment necessary to obtain the desired level of distraction.

Notably, if the implant 100 and/or corresponding differently-sized implants are to be implanted at multiple levels of a spine, they need not necessarily be deployed to the same degree. The implant size and the appropriate degree of deployment may be made selected for each vertebral level that is to be stabilized.

Figure 6:
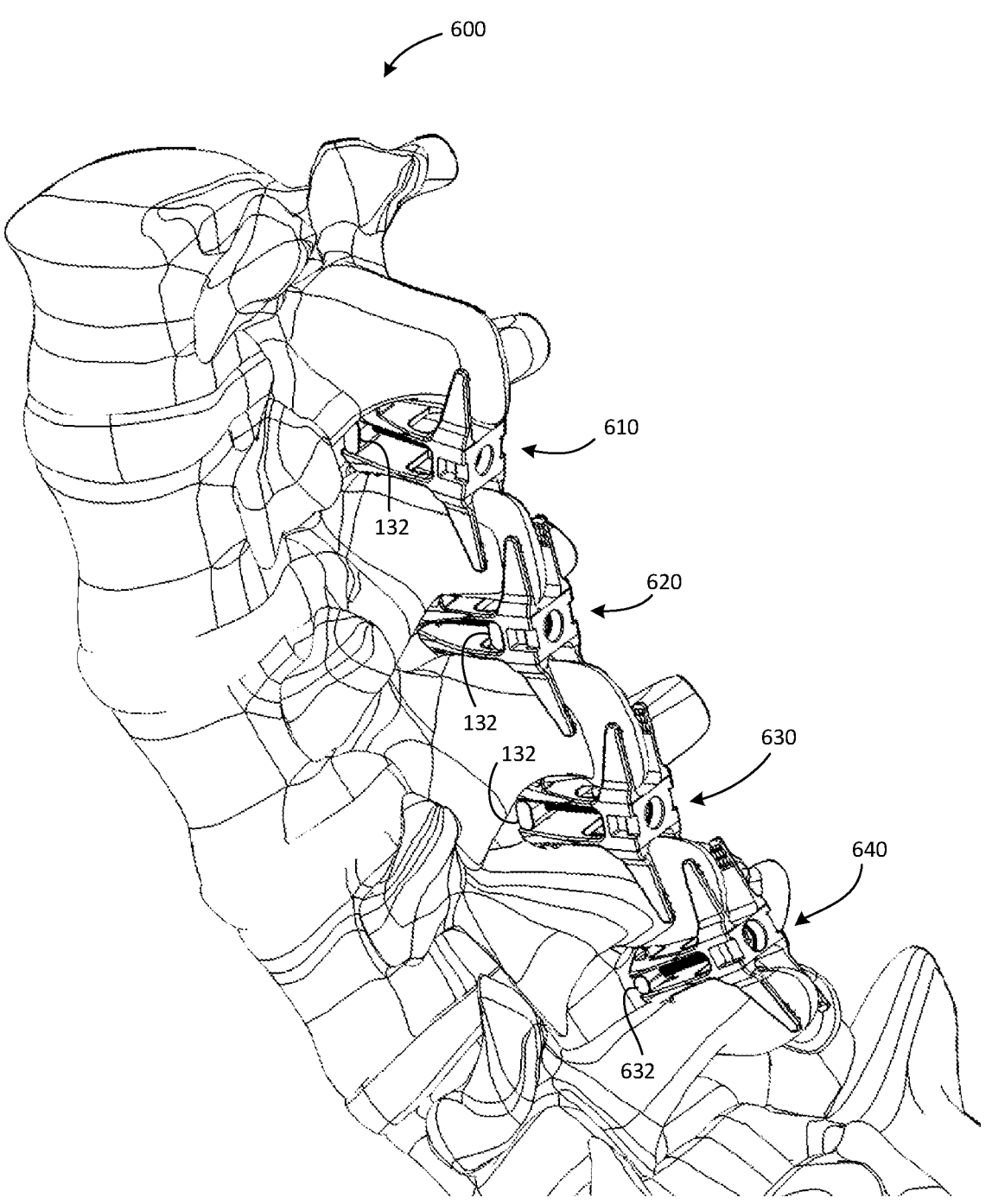
FIG. 6 is a perspective view of a spine with the implant of FIGS. 1A, 1B, 1C, and 1D implanted in four adjacent levels, according to one embodiment of the present disclosure.

FIG. 6 is a perspective view of a spine with the implant 100 of FIGS. 1A, 1B, 1C, and 1D implanted in four adjacent levels of a spine 600, according to one embodiment of the present disclosure. The implant 100 may be embodied in differing sizes, providing an implant 610, an implant 620, an implant 630, and an implant 640.

The implant 610, the implant 620, and the implant 630 may all closely resemble the implant 100, with a threaded block 132 that has an elongated cross-sectional shape along the superior-inferior direction. As shown, the implant 610 and the implant 630 are deployed, while the implant 620 remains in the retracted configuration.

The implant 640 may be smaller than the implant 610, the implant 620, and the implant 630, at least in the superior-inferior direction. Thus, the implant 640 may have a threaded block 632 with a cross-sectional shape that is generally circular, and is thus more compact in the superior-inferior direction than the threaded block 132. The implant 640 may thus have a lesser degree of expansion upon deployment than the implant 610, the implant 620, and the implant 630. The size and degree of deployment of each implant 610, 620, 630, 640 may be selected to obtain the desired level of distraction, preserving the desired level of lordosis or kyphosis along the length of the spine 600.

In some instances, where adjacent spinal levels are to be decompressed and stabilized, the implants may be sequentially placed to the appropriate depth that avoids interference of any of the superior wings 126 with any of the inferior wings 128 of adjacent implants. In some embodiments, one or more implants may be flipped vertically to avoid such interference.

Figure 7:
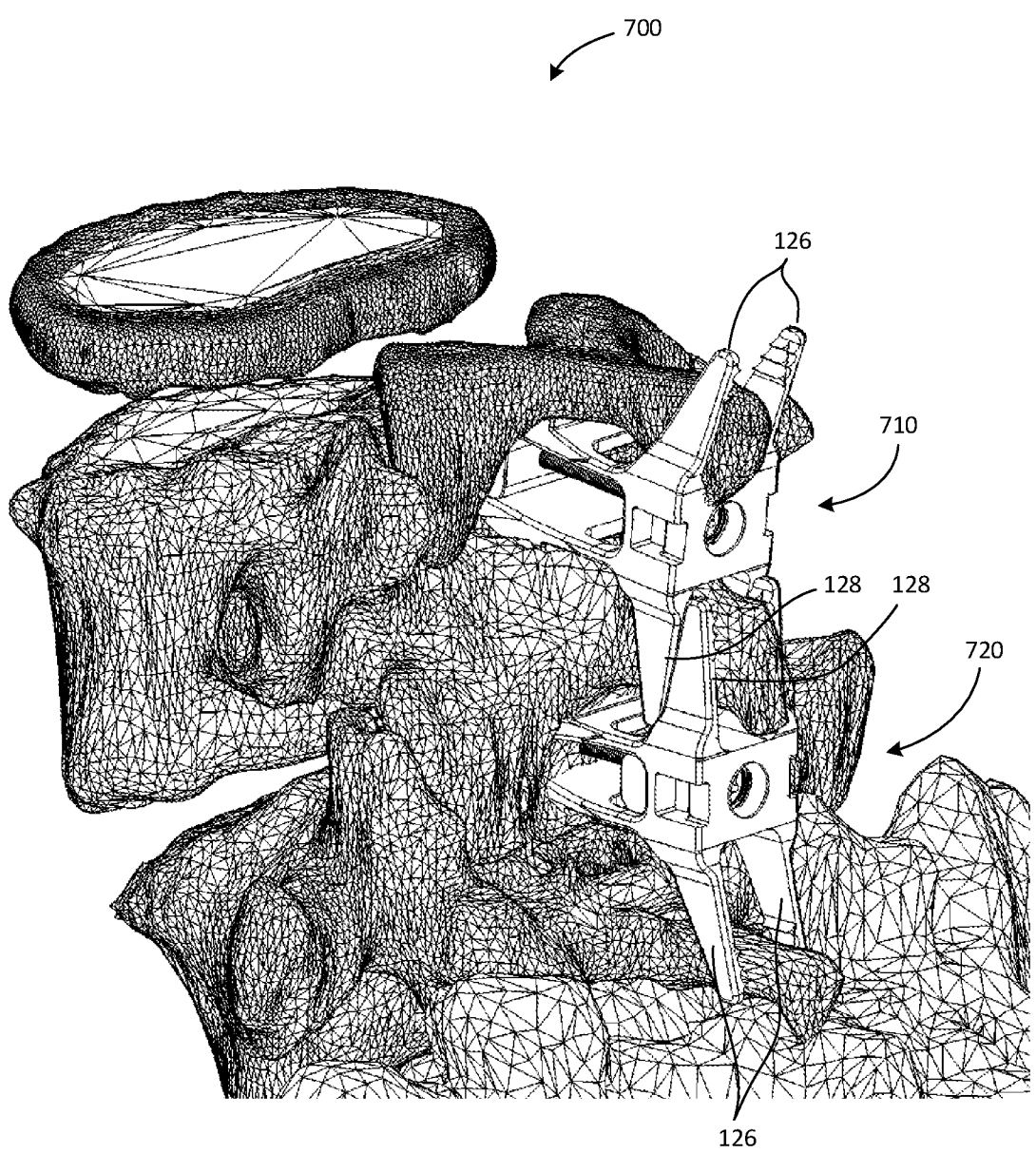
FIG. 7 is a perspective view of a spine with the implant of FIGS. 1A, 1B, 1C, and 1D implanted in two adjacent levels in opposite orientations to avoid interference with each other, according to one embodiment of the present disclosure.
Figures 8A, 8B, 8C, 8D:
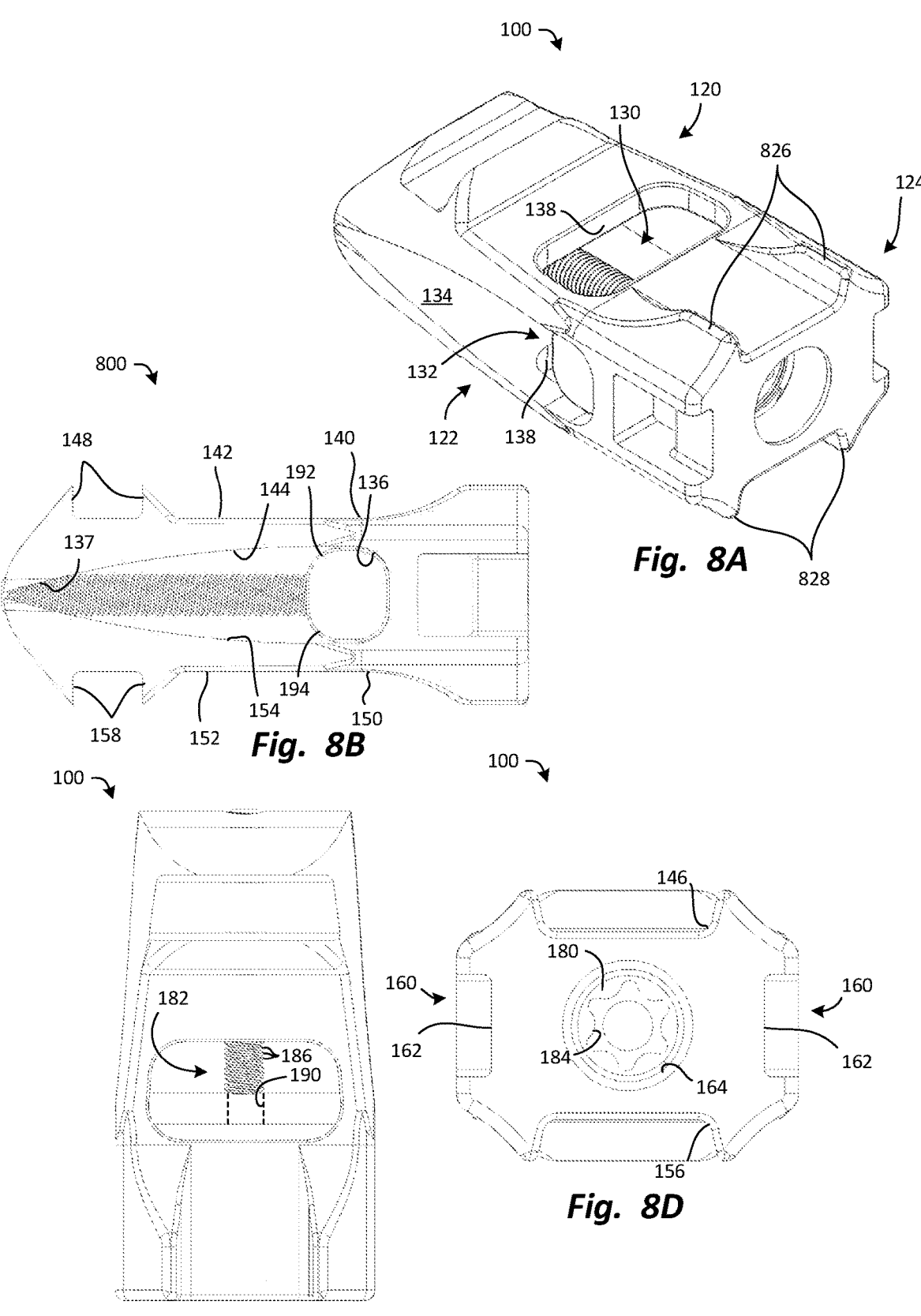
FIGS. 8A, 8B, 8C, and 8D are perspective, side elevation, plan, and rear elevation views of an interspinous-interlaminar implant according to another embodiment of the present disclosure, in a retracted configuration.

FIG. 7 is a perspective view of a spine 700 with the implant 100 of FIGS. 1A, 1B, 1C, and 1D implanted in two adjacent levels in opposite orientations to avoid interference with each other, according to one embodiment of the present disclosure. The implant 100 may be embodied as an implant 710 and an implant 720 placed at the level immediately below the implant 710. As shown, the implant 710 may be oriented as shown in FIG. 1A, while the implant 720 may be turned upside-down so that the inferior wings 128 of the implant 720 are on top, and grip the same spinous process as the inferior wings 128 of the implant 710 above. In this manner, the implant 720 may sufficiently grip the spinous process superior to it without interfering with the inferior wings 128 of the implant 710.

Notably, presence of the superior wings 126 and the inferior wings 128 is optional. In some embodiments, the superior wings 126 and the inferior wings 128 may be omitted in order to facilitate a less invasive, or even minimally invasive, surgical approach.

FIGS. 8A, 8B, 8C, and 8D are perspective, side elevation, plan, and rear elevation views of an interspinous-interlaminar implant, or implant 800, according to another embodiment of the present disclosure, in a retracted configuration. The implant 800 is configured similarly to the implant 100 of FIGS. 1A, 1B, 1C, and 1D, except that the implant 800 lacks the superior wings 126 and the inferior wings 128. In place of the superior wings 126 and the inferior wings 128, the implant 800 has superior ridges 826 and inferior ridges 828 that extend generally in the proximal-distal direction.

Like the superior wings 126 and the inferior wings 128, the superior ridges 826 and the inferior ridges 828 may help to retain the superior spinous process 90 and the inferior spinous process 92 in the superior concavity 146 and the inferior concavity 156, respectively. If desired, sutures cerclage cables, mechanical fasteners, or other attachment devices may be used to further secure the implant in place between the superior spinous process-lamina and the inferior spinous process-lamina. In some examples, such attachment devices may be passed around or through the superior spinous process 90, the superior lamina 94, the inferior spinous process 92 and/or the inferior lamina 96.

Absence of the superior wings 126 and the inferior wings 128 may make the implant significantly smaller than the implant 100, so that the implant 800 can be percutaneously delivered to the space between the superior spinous process-lamina and the inferior spinous process-lamina. Thus, some of the exposure and resection steps set forth above for implantation of the implant 100 may not be needed for the implant 800. Rather, the implant 800 may be delivered through a cannula. Such a cannula may be incorporated into a dilator, such as a sequential dilation system with successively larger cannulas that can be placed in enlarging succession to retract the tissues posterior to the implantation site.

Figure 9A:
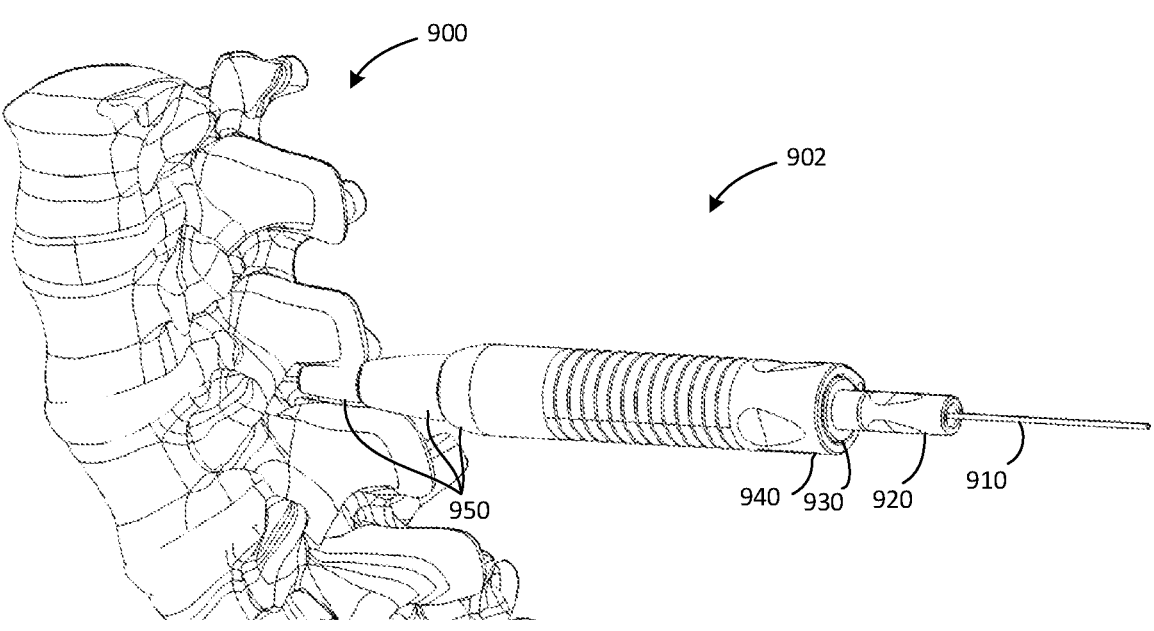
FIGS. 9A and 9B are perspective views of dilation of soft tissues to access the interspinous process and interlaminar space, and insertion of the implant of FIGS. 8A, 8B, 8C, and 8D in a retracted configuration, respectively, according to one embodiment of the present disclosure.
Figure 9B:
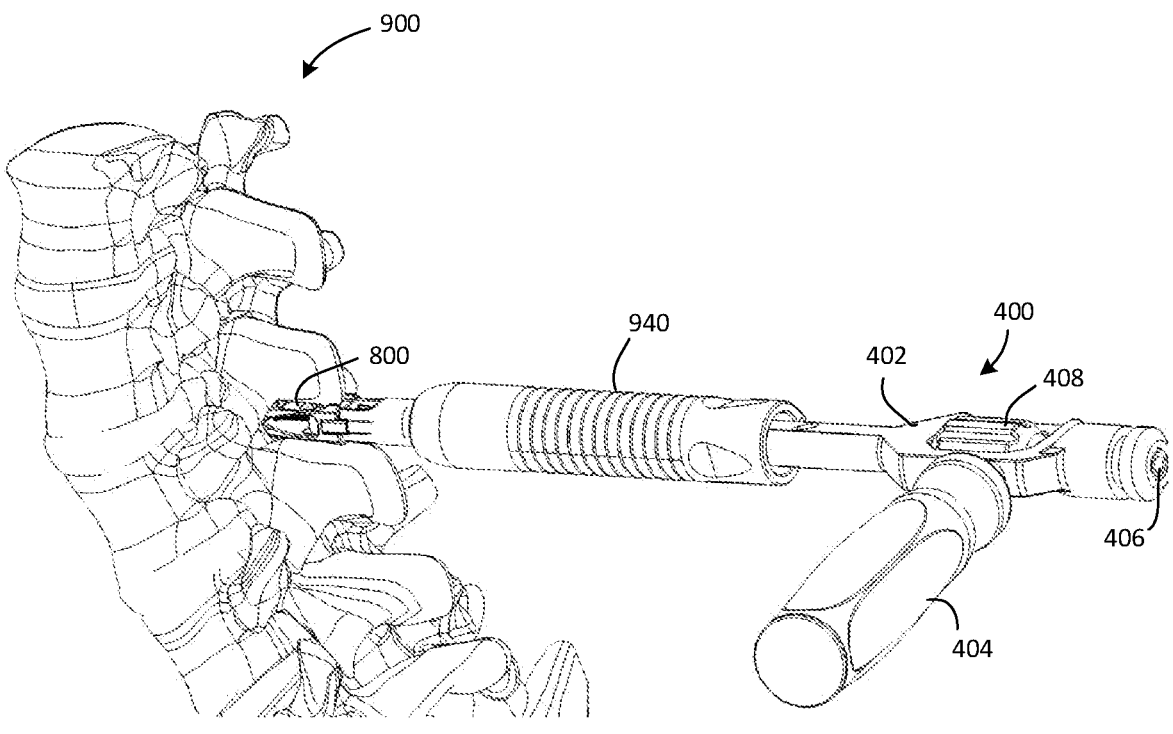

FIGS. 9A and 9B are perspective views of dilation of soft tissues to access the interspinous process-interlaminar space of a spine 900, and insertion of the implant 800 of FIGS. 8A, 8B, 8C, and 8D in a retracted configuration, respectively, according to one embodiment of the present disclosure. As shown, a dilator 902 may be used to access the surgical site. The dilator 902 may be placed over a K-wire 910.

As shown in FIG. 9A, the dilator 902 may have a first cannula 920, a second cannula 930, and a third cannula 940. The first cannula 920 may have a bore sized to receive the K-wire 910. The second cannula 930 may have a bore sized to receive the first cannula 920. The third cannula 940 may have a bore sized to receive the second cannula 930.

Thus, the K-wire 910 may first be anchored in the bone or soft tissue proximate the implantation site. Then, the first cannula 920 may be inserted over the K-wire 910 so that the K-wire 910 is received in the first cannula 920. The second cannula 930 may be inserted over the first cannula 920 so that the first cannula 920 and the K-wire 910 are received in the second cannula 930. The third cannula 940 may be inserted over the second cannula 930 so that the second cannula 930, the first cannula 920, and the K-wire 910 are received in the third cannula 940. The first cannula 920, the second cannula 930, and the third cannula 940 may each have a tapered tip 950 designed to gently penetrate soft tissues as the cannulas are pressed toward the implantation site.

Once the third cannula 940 has been placed, the second cannula 930, the first cannula 920, and the K-wire 910 may be withdrawn, and the third cannula 940 may be used to prepare the implantation site and insert the implant 800. If desired, any of the steps set forth above in the discussion of surgical methods for the implant 100 may be used. The probe 300 and the rasp trial 350 may also be used. The inserter 400 used to insert the implant 100 may also be used to install the implant 800 through the third cannula 940 in the retracted configuration. This is shown in FIG. 9B.

As shown in FIG. 9B, the implant 800 may be coupled to the inserter 400 as described in connection with the implant 100. Then, the inserter 400 may be gripped (for example, at the handle 404), and maneuvered to insert the implant 800 through the bore of the third cannula 940 and to the implantation site. The implant 800 may be positioned as desired, and optionally, partially, or fully deployed in a manner similar to that of the implant 100.

Figure 10A:
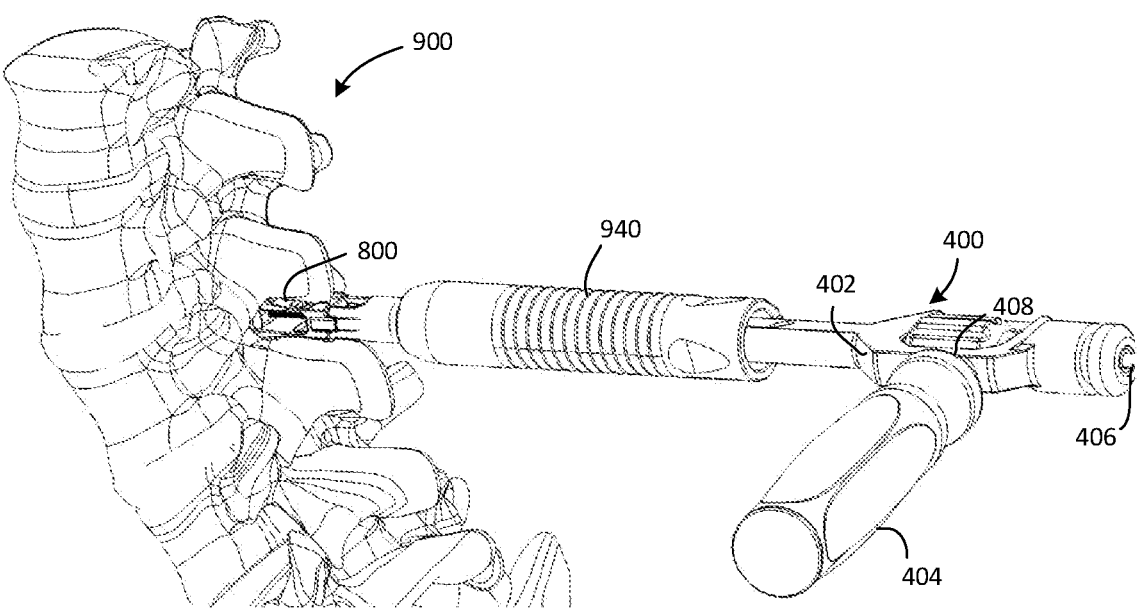
FIGS. 10A and 10B are perspective views of the implant of FIGS. 8A, 8B, 8C, and 8D in a deployed configuration in the interspinous process and interlaminar space, and a spine with the implant of FIGS. 8A, 8B, 8C, and 8D implanted in four adjacent levels, respectively, according to one embodiment of the present disclosure.
Figure 10B:
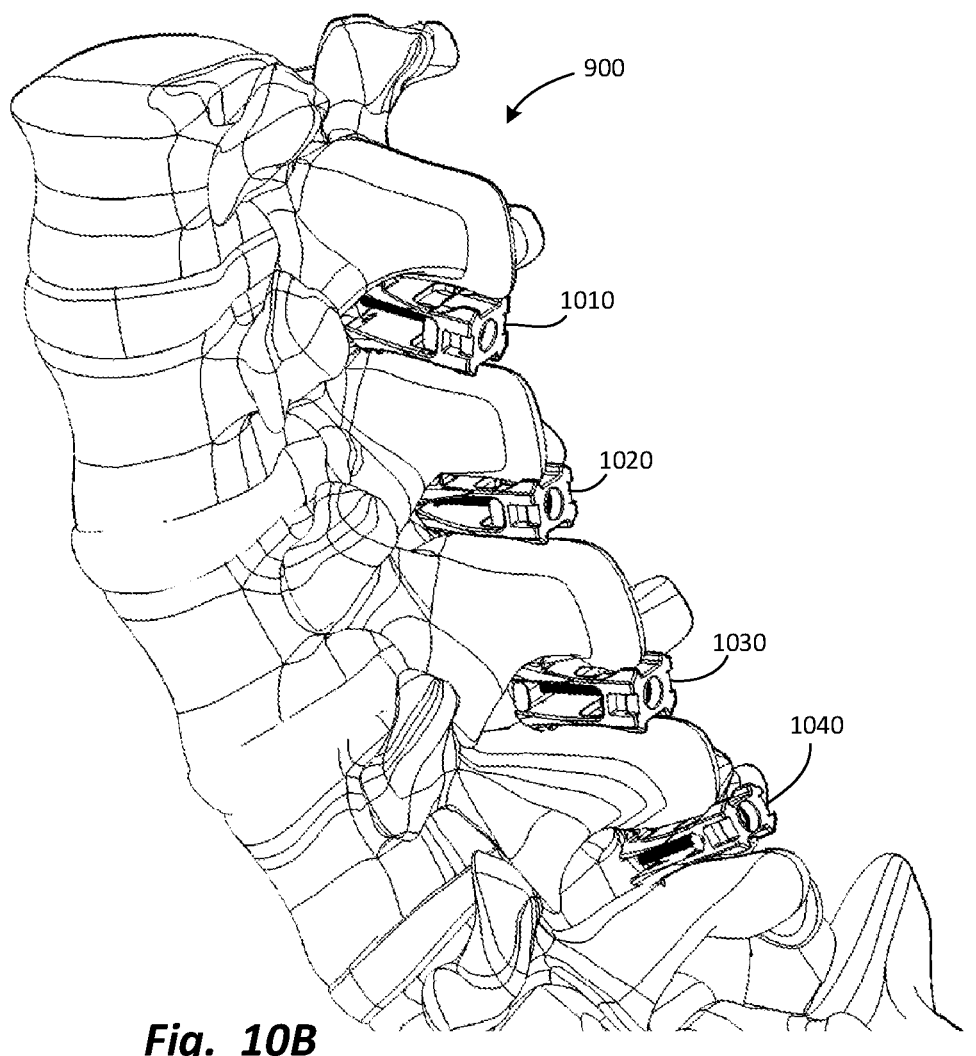

FIGS. 10A and 10B are perspective views of the implant 800 of FIGS. 8A, 8B, 8C, and 8D in a deployed configuration in the interspinous process-interlaminar space, and a spine 900 with the implant 800 of FIGS. 8A, 8B, 8C, and 8D implanted in four adjacent levels, respectively, according to one embodiment of the present disclosure. Like the implant 100, the implant 800 may be implanted in various sizes and degrees of deployment. FIG. 10A illustrates deployment of the implant 800 inserted through the third cannula 940.

FIG. 10B illustrates the implant 800, embodied as an implant 1010, an implant 1020, an implant 1030, and an implant 1040, used to treat four adjacent levels of the spine 900. For example, the implant 1010, the implant 1020, and the implant 1040 have all been left in the retracted configuration, while the implant 1030 has been deployed. The implant 1040 is of a more compact size, at least in the superior-inferior direction, than the implant 1010, the implant 1020, and the implant 1030.

Figures 11A, 11B:
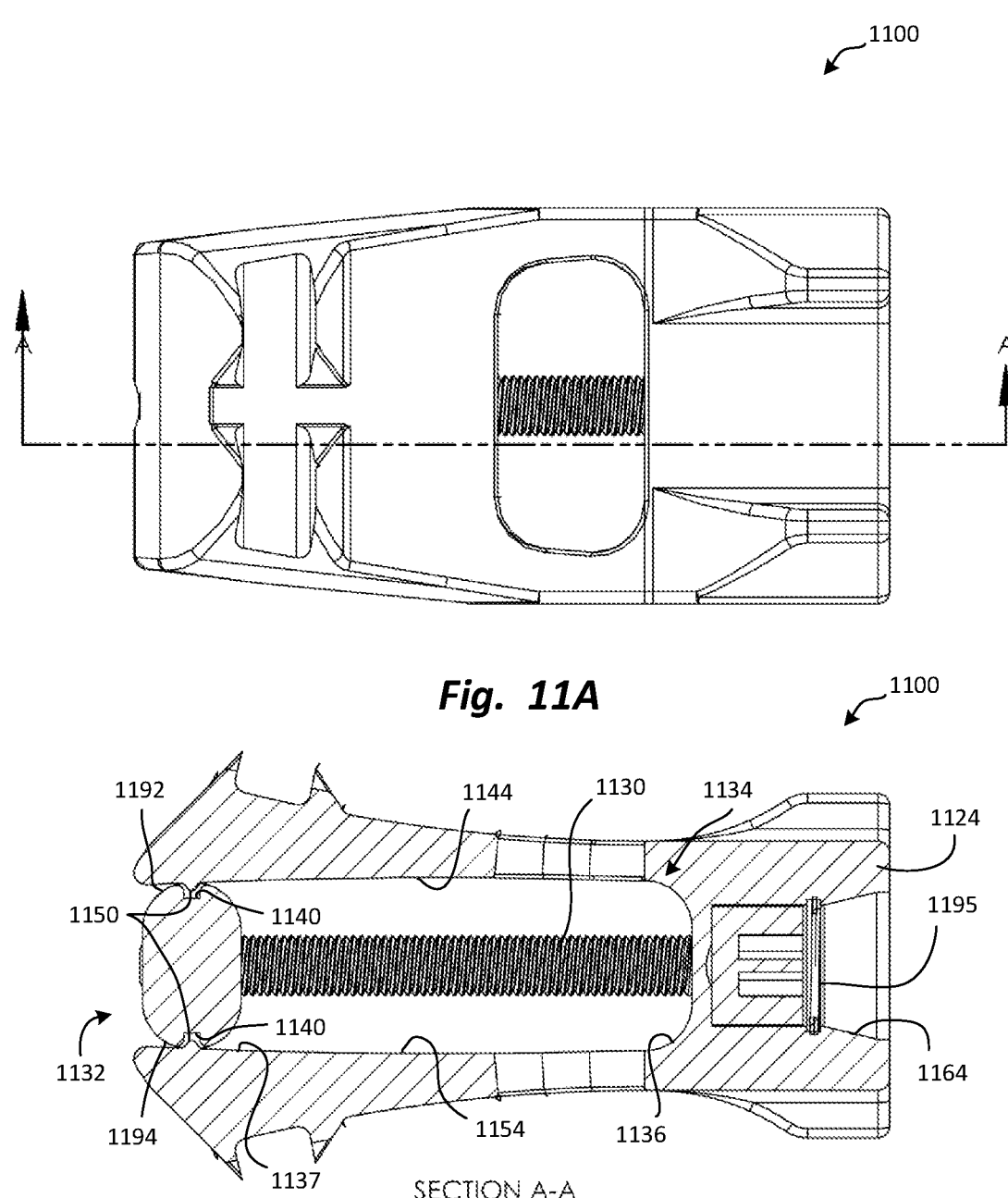
FIGS. 11A and 11B are top plan and side elevation, section views of another interspinous-interlaminar implant according to another embodiment of the present disclosure, in a deployed state.

FIGS. 11A and 11B are top plan and side elevation, section views of another interspinous-interlaminar implant, or implant 1100, according to another embodiment of the present disclosure, in a deployed state. The implant 1100 may be configured substantially the same as the implant 800 of FIGS. 8A, 8B, 8C, and 8D, except that the implant 1100 may have a threaded block 1132 and a cavity 1134 that have been modified to provide tactile and/or auditory confirmation of full deployment, and retain the implant 1100 in the fully deployed configuration.

More specifically, the cavity 1134 may have a proximal end 1136 and a distal end 1137, with an interior superior surface 1144 and an interior inferior surface 1154 that define the superior and inferior boundaries, respectively, of the cavity 1134. The interior superior surface 1144 and the interior inferior surface 1154 may each have a detent feature, such as a bump 1150, that protrudes interiorly.

The threaded block 1132 may have a superior surface 1192 and an inferior surface 1194 that engage the interior superior surface 1144 and the interior inferior surface 1154, respectively, as the threaded block 1132 moves from the proximal end 1136 toward the distal end 1137. The superior surface 1192 and the inferior surface 1194 may each have a detent feature that cooperates with the detent features of the cavity 1134. These detent features may be notches 1140 that receive the bumps 1150 of the superior surface 1192 and the inferior surface 1194 when the threaded block 1132 has moved fully to the distal end 1137, causing full deployment of the implant 1100.

Entry of bumps 1150 into the notches 1140 may be heard and/or felt by the surgeon as an audible and/or tactile "click." Further, entry of the bumps 1150 into the notches 1140 may provide a dwell point that restricts further motion of the threaded block 1132 along the length of the cavity 1134, thus avoiding over-deployment of the implant 1100.

In alternative embodiments, a wide variety of alternative detent features may be used to provide such auditory and/or tactile feedback and/or such a dwell point. For example, the bumps 1150 and notches 1140 may be reversed so that bumps 1150 are on the threaded block 1132 and notches 1140 are formed in the interior superior surface 1144 and the interior inferior surface 1154. In other embodiments, multiple detent points may be used. For example, with the notches 1140 on the threaded block 1132, multiple sets of bumps 1150 may be formed on the interior superior surface 1144 and the interior inferior surface 1154 such that there are multiple "clicks" that occur as the implant 1100 is deployed. If desired, smaller bumps 1150 may be provided proximal to the distal end 1137 of the cavity 1134, such that the corresponding dwell points can be overcome by further actuation of the threaded block 1132, until the threaded block 1132 reaches the distal end 1137.

Further, a snap ring 1195 or other structure may be used to retain the threaded member 1130 relative to the interconnecting member 1124. During assembly, the snap ring 1195 may optionally be inserted into the rear aperture 1164 after insertion of the threaded member 1130 into the rear aperture 1164. The snap ring 1195 may be a split ring, helical ring, or other expandable structure that can be compressed to fit beyond an undercut defined in the rear aperture 1164, and then allowed to expand such that it cannot be withdrawn in the absence of deliberate re-compression, thus preventing inadvertent disassembly of the implant 1100.

Figures 12A, 12B:
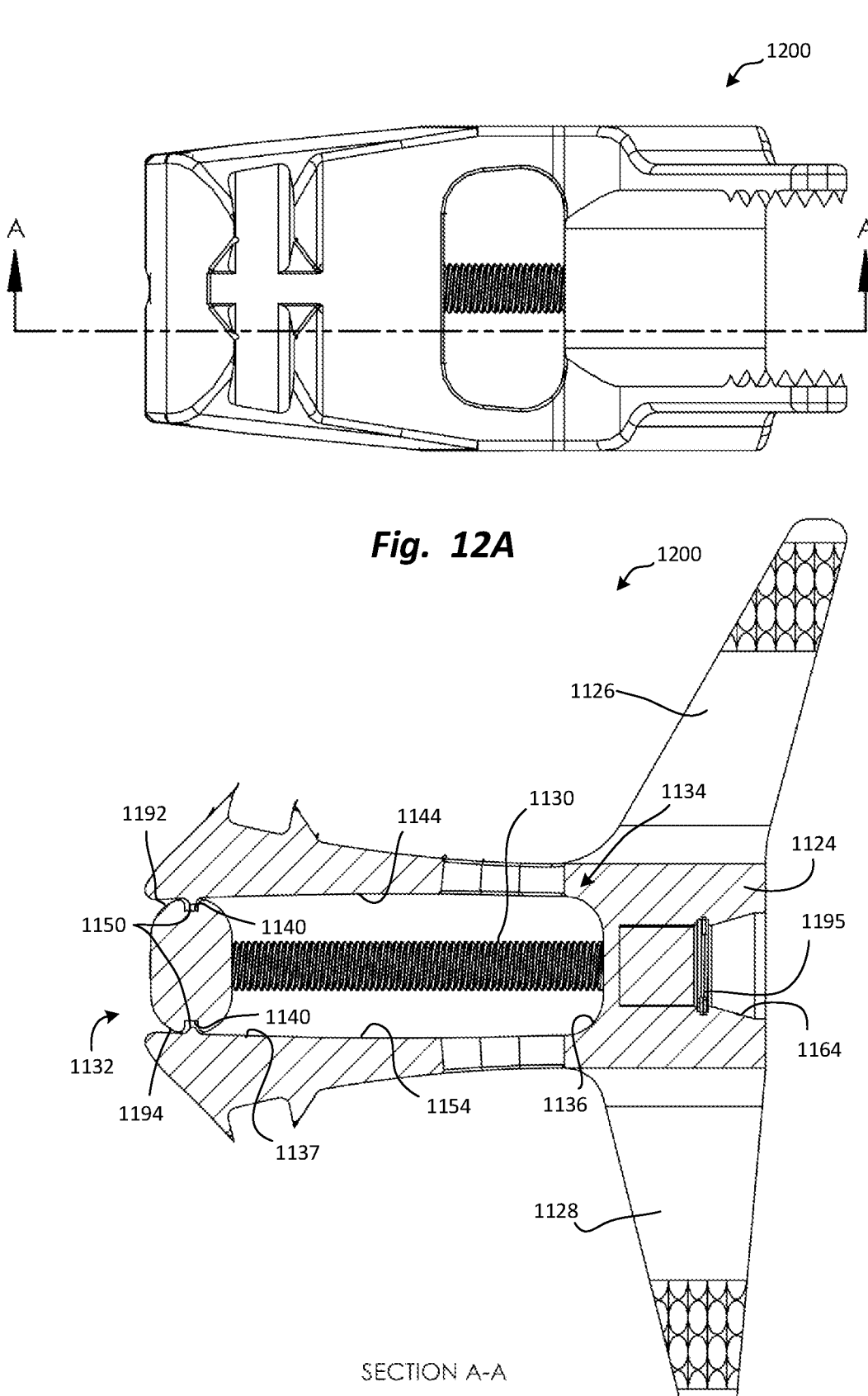
FIGS. 12A and 12B are top plan and side elevation, section views of yet another interspinous-interlaminar implant according to another embodiment of the present disclosure, in a deployed state.
Figures 13A, 13B, 13C, 13D:
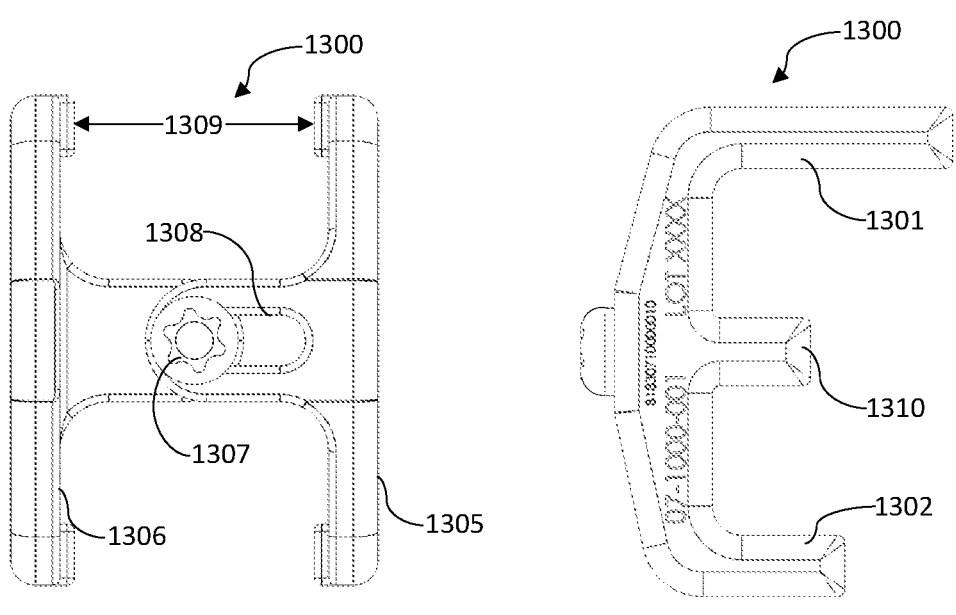
FIGS. 13A, 13B, 13C and 13D are front, side, perspective, and exploded perspective views of an interspinous-interlaminar implant clamp according to one embodiment of the present disclosure.

FIGS. 12A and 12B are top plan and side elevation, section views of yet another interspinous-interlaminar implant, or implant 1200, according to another embodiment of the present disclosure, in a deployed state. The implant 1200 may be configured substantially the same as the implant 100 of FIGS. 1A, 1B, 1C, and 1D, except that the implant 1200 may have a threaded block 1132 and a cavity 1134 that have been modified to provide tactile and/or auditory confirmation of full deployment, and retain the implant 1200 in the fully deployed configuration. These features may function substantially as described in connection with the implant 1100. Unlike the implant 1100, the implant 1200 may have superior wings 1126 and inferior wings 1128 like those of the implant 100.

FIGS. 13A, 13B, 13C and 13D are front, side, perspective, and exploded perspective views of an interspinous-interlaminar implant clamp, or clamp 1300, according to one embodiment of the present disclosure. The clamp 1300 may be configured to engage two superior wings and/or two inferior wings of an implant, for example the implant 100, the implant 1200, and/or the implant 1500, to prevent disengagement of the two superior wings and/or two inferior wings from the superior spinous process and/or inferior spinous process.

The clamp 1300 may include a first portion 1305, a second portion 1306 and a fastener 1307. The fastener 1307 may be configured to securely couple the first portion 1305 and the second portion 1306 to each other to restrict relative motion between the first portion 1305 and the second portion 1306. The fastener 1307 may be threaded or may incorporate other attachment methods known in the art. The fastener 1307 may extend generally along the proximal-distal direction.

The clamp 1300 may further include two superior arms, including a first superior arm 1301 and a second superior arm 1303, configured to engage the two superior wings, including a first superior wing 1501 and a second superior wing 1503, to prevent disengagement of the two superior wings from the superior spinous process. The clamp 1300 may also include two inferior arms, including a first inferior arm 1302 and a second inferior arm 1304, configured to engage the two inferior wings, including a first inferior wing 1502 and a second inferior wing 1504, to prevent disengagement of the two inferior wings from the inferior spinous process.

A first portion 1305 may include a first central member 1316 with a slot 1308 which, in conjunction with the fastener 1307, may facilitate adjustment of a distance between the first and second portions 1309 prior to securely coupling the first portion 1305 and the second portion 1306 with the fastener 1307.

The first portion may further include a first superior arm 1301, a first inferior arm 1302, and a first locating tab 1310 each extending distally from a first central member 1316. The second portion may also include a second superior arm 1303, a second inferior arm 1304, and a second locating tab 1311 each extending distally from a second central member 1317.

Further, the first superior arm 1301 may include a first superior arm tab 1312 and the first inferior arm 1302 may include a first inferior arm tab 1313 each extending laterally toward the second portion 1306.

The second superior arm 1303 may include a second superior arm tab 1314 and the second inferior arm 1304 may include a second inferior arm tab 1315 each extending laterally toward the first portion 1305.

The first superior arm tab 1312 may be configured to engage a first superior wing 1501 and the second superior arm tab 1314 may be configured to engage a second superior wing 1503 to prevent the first superior arm 1301 and the second superior arm 1303 from disengaging the first superior wing 1501 and the second superior wing 1503 through translation in a proximal direction.

The first inferior arm tab 1313 may be configured to engage a first inferior wing 1502 and the second inferior arm tab 1315 may be configured to engage a second inferior wing 1504 to prevent the first inferior arm 1302 and the second inferior arm 1304 from disengaging the first inferior wing 1502 and the second inferior wing 1504 through translation in a proximal direction.

The clamp 1300 may be formed of any known biocompatible materials, including but not limited to biocompatible metals such as Titanium and Titanium alloys, shape memory alloys such as Nitinol, biocompatible ceramics, and biocompatible polymers such as Polyether ether ketone (PEEK).

A clamp 1300 may be configured to securely connect to an interspinous-interlaminar implant, such as implant 100, implant 1200, and/or implant 1500. A clamp 1300 may be configured such that a first locating tab 1310 is slidably connectable to a first lateral aperture 1512 and a second locating tab is slidably connectable to a second lateral aperture 1513.

A clamp 1300 may be configured to engage an implant 1500 and may ensure secure engagement of the first superior wing 1501 and second superior wing 1503 with superior spinous process 90. Further, a clamp 1300 may be configured to engage an implant 1500 and may ensure secure engagement of the first inferior wing 1502 and second inferior wing 1504 with inferior spinous process 92.

A clamp 1300 may include a first superior arm 1301 configured to engage a first superior wing 1501. A first superior arm 1301 may include a first superior arm tab 1312 to prevent the first superior arm 1301 from sliding off the first superior wing 1501. A clamp 1300 may include a first inferior arm 1302 configured to engage a first inferior wing 1502. A first inferior arm 1302 may include a first inferior arm tab 1313 to prevent the first inferior arm 1302 from sliding off the first inferior wing 1502.

A clamp 1300 may include a second superior arm 1303 configured to engage a second superior wing 1503. A second superior arm 1303 may include a second superior arm tab 1314 to prevent the second superior arm 1303 from sliding off the second superior wing 1503. A clamp 1300 may include a second inferior arm 1304 configured to engage a second inferior wing 1504. A second inferior arm 1304 may include a second inferior arm tab 1315 to prevent the second inferior arm 1304 from sliding off the second inferior wing 1504.

FIGS. 14A, 14B, 14C and 14D are front, side, perspective, and exploded perspective views of an interspinous-interlaminar implant clamp, or clamp 1400, according to another embodiment of the present disclosure. The clamp 1400 is configured similarly to the clamp 1300 of FIGS. 13A, 13B, 13C, and 13D, including a fastener 1407, a first portion 1405 and a second portion 1406, except that the clamp 1400 may include an extended first central member 1416 and/or an extended second central member 1417. The extended first central member 1416 may include a slot 1408 that is longer than a slot 1308 shown in another embodiment. The slot 1408 in conjunction with an extended first central member 1416 and/or an extended second central member 1417 may allow a greater distance between first and second portions 1409 and thus may be compatible with a greater size range of interspinous-interlaminar implants.

Figures 15A, 15B, 15C:
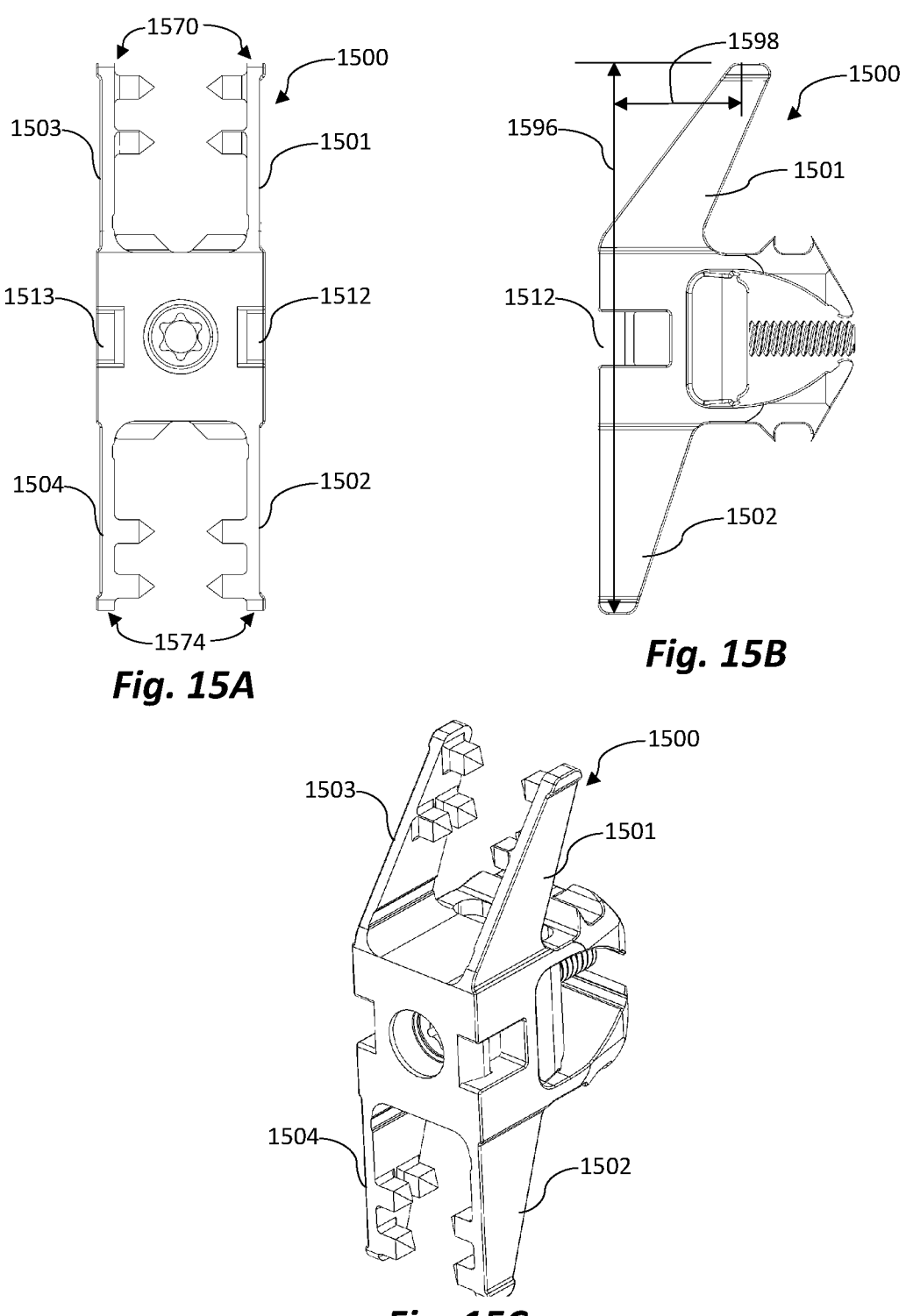
FIGS. 15A, 15B and 15C are front, side, and perspective views of an interspinous-interlaminar implant according to another embodiment of the present disclosure, in a retracted configuration.

FIGS. 15A, 15B and 15C are front, side, and perspective views of an interspinous-interlaminar implant, or implant 1500, according to another embodiment of the present disclosure, in a retracted configuration. The implant 1500 is configured similarly to the implant 100 of FIGS. 1A, 1B, 1C, and 1D. Advantageously, the superior tips 1570 may be displaced, along the proximal-distal direction, from the inferior tips 1574. As shown, the inferior tips 1574 may be separated from the superior tips 1570 by a superior-inferior displacement 1596, and by a proximal-distal displacement 1598. The proximal-distal displacement 1598 may be sufficient to provide some flexibility whereby the implant 1500 can be implanted in the orientation shown in FIG. 15C, or reversed so that the first superior wing 1501 and second superior wing 1503 grip the inferior spinous process 92 and the first inferior wing 1502 and second inferior wing 1504 grip the superior spinous process 90. Notably, use of the terms "superior" and "inferior" in relation to the implants described herein does not imply any required orientation upon implantation.

FIGS. 16A, 16B and 16C are front, side, and perspective views of an interspinous-interlaminar implant, implant 1500, and interspinous-interlaminar implant clamp, clamp 1400, assembled according to one embodiment of the present disclosure, in a retracted configuration. An interspinous-interlaminar implant system may include an implant 1500 and a clamp 1400. The system may be configured to maintain spacing between a superior spinous process and a superior lamina, and an inferior spinous process and an inferior lamina, of adjacent vertebrae of a spine. In an embodiment, the clamp 1400 may be configured to engage the implant 1500 to prevent deflection of one or more pairs of wings of the implant 1500 away from a portion of bone.

Insertion of the implant 1500 may be commenced by slightly spreading the first superior wing 1501 and second superior wing 1503 and/or the first inferior wing 1502 and second inferior wing 1504 with pliers or another tool, at the mid-portion of each of the superior wings and/or the inferior wings, to ensure the appropriate depth of insertion. The implant 1500 may be introduced via impaction utilizing a mallet, for example, by striking the proximal end of the inserter 400 with the implant 1500 coupled to the inserter 400. In some embodiments, a handle (not shown) may be secured to the proximal end 430 to facilitate impaction.

The implant 1500 may then be expanded by rotating the drive rod 406 clockwise until a tactile click are felt. Proper depth may be determined if a beaded tip probe can be passed freely, leaving a 3-4 mm separation from the dura. If the implant 1500 is not seated appropriately, further resurfacing or slightly more impaction force may be utilized. If the first superior wing 1501, second superior wing 1503, first inferior wing 1502 and/or the second inferior wing 1504 do not have sufficient bony contact, additional stability may be achieved by slightly crimping the first superior wing 1501 with the second superior wing 1503 and/or crimping the first inferior wing 1502 with the second inferior wing 1504, as appropriate. In one embodiment, a clamp 1400 may then be secured to an implant 1500 after the implant 1500 is inserted and expanded as described and a fastener 1407 may be engaged to secure the first portion 1405 and second portion 1406 in position.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

What is claimed is:

1. A system configured to maintain spacing between a superior spinous process and a superior lamina, and an inferior spinous process and an inferior lamina, of adjacent vertebrae of a spine in a body of a patient, the system comprising:

an implant comprising:

a first superior wing and a second superior wing extending superiorly from a proximal superior surface of the implant such that, in an implanted position, the first superior wing and the second superior wing are configured to engage the superior spinous process therebetween; and a first inferior wing and a second inferior wing extending inferiorly from a proximal inferior surface of the implant such that, in the implanted position, the first inferior wing and the second inferior wing are configured to engage the inferior spinous process therebetween; and a clamp configured to be implanted in the body, comprising:

a first portion configured to engage a first side of the implant;

a second portion configured to engage a second side of the implant;

a fastener configured to securely couple the first portion and the second portion;

a first superior arm and a second superior arm configured to engage the first superior wing and the second superior wing to prevent disengagement of the first superior wing and the second superior wing from the superior spinous process; and a first inferior arm and a second inferior arm configured to engage the first inferior wing and the second inferior wing to prevent disengagement of the first inferior wing and the second inferior wing from the inferior spinous process;

wherein:

the first superior arm and the first inferior arm are integrally formed with each other; and the second superior arm and the second inferior arm are integrally formed with each other.

2. The system of claim 1, wherein a distance between the first portion and the second portion is adjustable.

3. The system of claim 1, wherein the implant further comprises:

a first lateral aperture; and a second lateral aperture; and the clamp further comprises:

a first locating tab; and a second locating tab;

wherein the first locating tab is slidably connectable to the first lateral aperture and the second locating tab is slidably connectable to the second lateral aperture, thereby limiting translation of the clamp relative to the implant in a superior-inferior direction.

4. The system of claim 1, wherein:

the first superior arm comprises a first superior arm tab;

the first inferior arm comprises a first inferior arm tab;

the second superior arm comprises a second superior arm tab; and the second inferior arm comprises a second inferior arm tab;

wherein:

the first superior arm tab extends laterally toward the second superior arm;

the first inferior arm tab extends laterally toward the second inferior arm;

the second superior arm tab extends laterally toward the first superior arm; and the second inferior arm tab extends laterally toward the first inferior arm.

5. The system of claim 4, wherein the first superior arm tab and the second superior arm tab are configured to engage the first superior wing and the second superior wing to prevent the first superior arm and the second superior arm from disengaging the first superior wing and the second superior wing through translation in a proximal direction.

6. The system of claim 4, wherein the first inferior arm tab and the second inferior arm tab are configured to engage the first inferior wing and the second inferior wing to prevent the first inferior arm and the second inferior arm from disengaging the first inferior wing and the second inferior wing through translation in a proximal direction.

7. The system of claim 1, wherein the first superior arm and the second superior arm are longer than the first inferior arm and the second inferior arm.

8. A system configured to maintain spacing between a first bone and a second bone, the system comprising:
an implant comprising a first pair of wings configured to grip the first bone therebetween; and
a clamp configured to engage the first pair of wings to prevent deflection of the first pair of wings away from the first bone, the clamp comprising:
a first superior arm comprising a first superior arm tab;
a first inferior arm comprising a first inferior arm tab;
a second superior arm comprising a second superior arm tab; and
a second inferior arm comprising a second inferior arm tab
wherein:
the first superior arm tab extends laterally toward the second superior arm;
the first inferior arm tab extends laterally toward the second inferior arm;
the second superior arm tab extends laterally toward the first superior arm;
the second inferior arm tab extends laterally toward the first inferior arm;
the first superior arm and the first inferior arm are integrally formed with each other;
the second superior arm and the second inferior arm are integrally formed with each other;
the first pair of wings comprises a pair of superior wings extending superiorly from a proximal superior surface of the implant; and
the first superior arm tab and the second superior arm tab are configured to engage the pair of superior wings to prevent the first superior arm and the second superior arm from disengaging from the pair of superior wings through translation in a proximal direction.

9. The system of claim 8, wherein:
the implant further comprises a pair of inferior wings;
the first superior arm and the second superior arm are configured to engage the pair of superior wings to prevent disengagement of the pair of superior wings from the first bone; and
the first inferior arm and the second inferior arm are configured to engage the pair of inferior wings to prevent disengagement of the pair of inferior wings from the second bone.

10. The system of claim 8, wherein:
the implant further comprises a pair of inferior wings; and
the first inferior arm tab and the second inferior arm tab are configured to engage the pair of inferior wings to prevent the first inferior arm and the second inferior arm from disengaging from the pair of inferior wings through translation in a proximal direction.

11. The system of claim 8, wherein the clamp further comprises:
a first portion configured to engage a first side of the implant;
a second portion configured to engage a second side of the implant; and
a fastener configured to securely couple the first portion and the second portion.

12. The system of claim 8, wherein the clamp further comprises:

a first portion configured to engage a first side of the implant; and
a second portion configured to engage a second side of the implant;
wherein a distance between the first portion and the second portion is adjustable.

13. A system configured to maintain spacing between a superior spinous process and a superior lamina, and an inferior spinous process and an inferior lamina, of adjacent vertebrae of a spine, the system comprising:
an implant comprising:
a first superior wing and a second superior wing extending superiorly from a proximal superior surface of the implant such that, in an implanted position, the first superior wing and the second superior wing are configured to engage the superior spinous process therebetween; and
a first inferior wing and a second inferior wing extending inferiorly from a proximal inferior surface of the implant such that, in the implanted position, the first inferior wing and the second inferior wing are configured to engage the inferior spinous process therebetween; and a clamp comprising:
a first superior arm and a second superior arm configured to engage the first superior wing and the second superior wing to prevent disengagement of the first superior wing and the second superior wing from the superior spinous process; and
a first inferior arm and a second inferior arm configured to engage the first inferior wing and the second inferior wing to prevent disengagement of the first inferior wing and the second inferior wing from the inferior spinous process;
wherein:
the first superior arm comprises a first superior arm tab extending laterally toward the second superior arm;
the first inferior arm comprises a first inferior arm tab extending laterally toward the second inferior arm;
the second superior arm comprises a second superior arm tab extending laterally toward the first superior arm;
the second inferior arm comprises a second inferior arm tab extending laterally toward the first inferior arm;
the first superior arm and the first inferior arm are integrally formed with each other; and
the second superior arm and the second inferior arm are integrally formed with each other.

14. The system of claim 13, wherein the clamp further comprises:
a first portion configured to engage a first side of the implant; and
a second portion configured to engage a second side of the implant;
wherein a distance between the first portion and the second portion is adjustable.

15. The system of claim 13, wherein the clamp further comprises:
a first portion configured to engage a first side of the implant;
a second portion configured to engage a second side of the implant; and
a fastener configured to securely couple the first portion and the second portion.

16. The system of claim 13, wherein:
the implant further comprises:
a first lateral aperture; and
a second lateral aperture; and the clamp further comprises:

a first locating tab; and a second locating tab; and the first locating tab is slidably connectable to the first lateral aperture and the second locating tab is slidably connectable to the second lateral aperture, thereby limiting translation of the clamp relative to the implant in a superior-inferior direction.

17. The system of claim 13, wherein the first superior arm tab and the second superior arm tab are configured to engage the first superior wing and the second superior wing respectively to prevent the first superior arm and the second superior arm from disengaging the first superior wing and the second superior wing respectively through translation in a proximal direction.

18. The system of claim 13, wherein the first inferior arm tab and the second inferior arm tab are configured to engage the first inferior wing and the second inferior wing respectively to prevent the first inferior arm and the second inferior arm from disengaging the first inferior wing and the second inferior wing respectively through translation in a proximal direction.

19. The system of claim 13, wherein the first superior arm and the second superior arm are longer than the first inferior arm and the second inferior arm.

\* \* \* \* \*